(12) United States Patent
Gracia et al.

(10) Patent No.: US 6,753,436 B2
(45) Date of Patent: Jun. 22, 2004

(54) OLEFIN POLYMERIZATION CATALYSTS

(75) Inventors: Pascual Royo Gracia, Villalbilla (ES); Jesus Cano Sierra, Alcala de Henares (ES); Miguel Angel Flores De Paco, Aranjuez (ES); Begoña Peña Garcia, Madrid (ES)

(73) Assignee: Repsol Quimica, S.A., Madrid (ES)

( * ) Notice: Subject to any disclaimer, the term of this patent is extended or adjusted under 35 U.S.C. 154(b) by 0 days.

(21) Appl. No.: 10/052,476

(22) Filed: Jan. 18, 2002

(65) Prior Publication Data
US 2002/0115560 A1 Aug. 22, 2002

(30) Foreign Application Priority Data

Jan. 18, 2001 (EP) ............................................. 01500020

(51) Int. Cl.[7] .......................... C07F 17/00; B01J 31/00; C08F 4/64
(52) U.S. Cl. ......................... 556/11; 502/103; 502/117; 526/160; 526/943; 534/11; 534/15; 556/12; 556/43; 556/46; 556/52; 556/54; 556/58; 556/136; 556/137
(58) Field of Search ...................... 534/11, 15; 502/103, 502/117; 526/160, 943; 556/11, 12, 43, 46, 52, 54, 58, 136, 137

(56) References Cited

FOREIGN PATENT DOCUMENTS

| EP | 0 293 815 A1 | 12/1988 |
|---|---|---|
| EP | 0 416 815 A2 | 3/1991 |
| EP | 0 757 992 A1 | 2/1997 |
| EP | 0 839 834 A1 | 5/1998 |
| EP | 0 839 836 A1 | 5/1998 |
| EP | 0 953 580 A1 | 11/1999 |
| EP | 0 953 581 A1 | 11/1999 |
| EP | 0 839 836 B1 | 12/2000 |
| EP | 1 095 944 A1 | 5/2001 |
| EP | 0 839 834 B1 | 6/2001 |
| WO | 99/52949 | 10/1999 |

OTHER PUBLICATIONS

Amor, F., et al., "Zirconium and hafnium mono(alkyl) complexes containing a tridentate linked amido-tetramethylcyclopentadienyl $C_5Me_4SiMe_2NCH_2CH_2OCH_3)Cl_2$," Journal of Organometallic Chemistry, vol. 558, pp. 139–146 (1998).

Bertuleit, A., et al., "Developing a fulvene route to $C_1$-bridged 'constrained geometry' Ziegker catalyst systems," Topics in Catalysts, vol. 7, pp. 37–44 (1999).

Bertuleit, A., et al., "Uncovering Alternative Reaction Pathways Taken by Group 4 Metallocene Cations: Facile Intramolecular CH Activation of Cp–(Dimethylamino)alkyl Substituents by a Methylzirconocene Cation," Organometallics, vol. 16, pp. 2891–2899 (1997).

Duda, L., et al., "Formationof a Constrained–Geometry Ziegler Catalyst System Containing a $C_1$Instead of the Usual $Si_1$Connection Between the Cyclopentadienyl and Amido Ligand Components," Eur. J. Inorg. Chem., pp. 1153–1162 (1998).

(List continued on next page.)

Primary Examiner—Porfirio Nazario-Gonzalez
(74) Attorney, Agent, or Firm—Ladas & Parry

(57) ABSTRACT

The invention concerns olefin polymerization catalyst component comprising an organometallic compound of general formula I

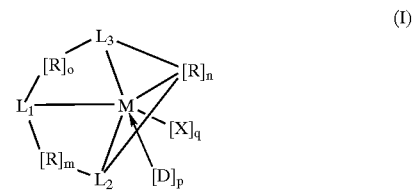

(I)

wherein:

M is a transition metal of groups 3, 4–10, lanthanide or actinide of the periodic table of the elements; each R is independently a structural bridge rigidly connecting two ligands $L_1$, $L_2$ and $L_3$ and is constituted by 1 to 4 chain atoms selected from carbon, silicon, germanium, oxygen, boron; m, n and o are 0 or 1, with the proviso that m+n+o is 2 or 3; $L_1$ is a ligand of the cyclopentadienyl type or is isolobal to cyclopentadienyl, $L_2$ is a ligand of the cyclopentadienyl type or is isolobal to cyclopentadienyl, or a monovalent anionic ligand selected from the group consisting of N, P, B when m+n=2, it is selected from the group consisting of $NR^1$, $PR^1$, $BR^1$, O and S when m+n=1;

$L_3$ is a monovalent anionic ligand selected from the group consisting of N, P, B when n+o=2, it is selected from the group consisting of $NR^1$, $PR^1$, $BR^1$, O and S when n+o=1; $R^1$ is hydrogen, $C_1$–$C_{20}$ alkyl, $C_3$–$C_{20}$ cycloalkyl, $C_6$–$C_{20}$ aryl, $C_3$–$C_{20}$ alkenyl, optionally comprising 1 to 5 hetetoatoms such as Si, N, P, O, F, Cl, Br; each X is independently selected from the group consisting of hydrogen, halogen, $NR^2_2$, $R^2$ with $R^2$ equal to $C_1$–$C_{20}$ alkyl, $C_1$–$C_{20}$ alkyl, $C_3$–$C_{20}$ cycloalkyl, $C_6$–$C_{20}$ aryl, $C_3$–$C_{20}$ alkenyl, optionally comprising 1 to 5 heteroatoms such as Si, N, P, O, F, Cl, Br; q is a number whose value is: 0, 1, 2 or 3, depending on the valence of the metal M; D is a neutral Lewis base, p is a number whose value is: 0, 1, 2 or 3.

The invention also concerns catalysts comprising compounds of formula (I) and the polymerization process making use of a catalyst comprising the claimed compounds.

26 Claims, No Drawings

OTHER PUBLICATIONS

Fedushkin, I.L., et al., "Organometallic Compounds of the Lanthanides. 141. Synthesis, Molecular Structure, and Solution Behavior of Some Lanthanum(III) and Ytterbium(II) Complexes Containg New Tridentate 1,2–and 1,3–Bis(2–(dimethylamino)ethyl) cyclopentadienyl Ligands," *Organometallics*, vol. 19, pp. 4066–4076 (2000).

Okuda, J., et al., "Synthesis and Characterization of Titanium Complexes Containing Potentially Tridentate Amido–Cyclopentadienyl Ligands," *Chem. Ber.*, vol. 129, pp. 275–277 (1996).

Rozell, Jr., J.M. and P.R. Jones, "Silenes and Silenoids. 9. The Synthesis of Polyfunctional Bis(group 14) –Substituted Cyclopentadienes via a Novel Cleavage Reaction of Silicon–Carbon Bonds by Chloride Ion," *Organometallics*, vol. 4, pp. 2206–2210 (1985).

OLEFIN POLYMERIZATION CATALYSTS

The present invention concerns new organometallic compounds and polymerization catalysts comprising the organometallic compounds.

During the last 20 years a lot of research has been carried out in order to establish the relation structure-reactivity in single site olefin polymerization catalysis. As a result, several information concerning the influence of the catalyst structure on molecular weight, tacticity and comonomer insertion are available today.

One of the first methods used for achieving a better control of the catalyst properties is the use of a bridge which renders two cyclopentadienyl ligands stereorigid. In this way, it has been possible to obtain highly isotactic and highly syndiotactic propylene polymers.

EP 416 815 discloses monocyclopentadienyl catalysts wherein a cyclopentadienyl ligand and an amido ligand are connected through a covalent bridge. The resulting catalyst can incorporate very efficiently long chain alpha-olefins.

In the last decade, a lot of effort have been dedicated to the development of these complexes and to the study of the influence of the ligand structure on catalyst activity.

SUMMARY OF THE INVENTION

It has been surprisingly found that it is possible to prepare organometallic compounds wherein a transition metal is bonded to three ligands which are rigidly connected through structural bridges, wherein at least one ligand is of the cyclopentadienyl type or is isolobal to cyclopentadienyl and the remainder(s) are monovalent anionic ligands. These complexes are effective catalysts for olefin polymerization. By varying the type of ligands and the structure of the two (or three) covalent bridges it is possible to modify the characteristics of the resulting catalyst in terms of molecular weight, comonomer incorporation and tacticity of the obtained polymer.

DESCRIPTION OF THE INVENTION

The organometallic catalysts of the invention are represented by general formula (I):

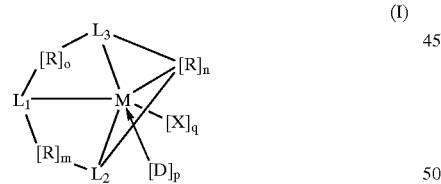

(I)

wherein:
- M is a transition metal of groups 3, 4–10, lanthanide or actinide of the periodic table of the elements, preferably titanium, zirconium or hafnium;
- each R is independently a structural bridge rigidly connecting two ligands $L_1$, $L_2$ and $L_3$ and is constituted by 1 to 4 chain atoms selected from carbon, silicon, germanium, oxygen, boron; these atoms can be part of fused rings, aromatic rings, aliphatic rings or spiro rings; preferred examples of groups R are: $CR^1_2$, $SiR^1_2$, $CR^1_2$—$CR^1_2$, $CR^1_2$—$SiR^1_2$, $SiR^1_2$—$SiR^1_2$;
- wherein each $R^1$ is independently selected from hydrogen, $C_1$–$C_{20}$ alkyl, $C_3$–$C_{20}$ cycloalkyl, $C_6$–$C_{20}$ aryl, $C_3$–$C_{20}$ alkenyl, optionally comprising 1 to 5 heteroatoms such as Si, N, P, O, F, Cl, Br, preferably $R^1$ is selected from $C_1$–$C_6$ linear or branched alkyls; most preferably is methyl, ethyl, isopropyl, tertbutyl;
- m, n and o are 0 or 1, with the proviso that m+n+o is 2 or 3;
- $L_1$ is a ligand of the cyclopentadienyl type or is isolobal to cyclopentadienyl, preferably a cyclopentadienyl, indenyl or fluorenyl ring, cyclopenteno[b]tiophenyl cyclopenteno[b:b']-dithiophenyl cyclopenteno[b]pyrrolyl, boratabenzene, phospholyl, dihydroindeno[b]indolyl, optionally substituted by one or more $R^1$ groups; most preferably a cyclopentadienyl, indenyl or fluorenyl ring, optionally substituted by one or more $R^1$ groups;
- $L_2$ is a ligand defined as $L_1$, or a monovalent anionic ligand selected from the group consisting of N, P, B when m+n=2, from the group consisting of $NR^1$, $PR^1$, $BR^1$, O and S when m+n=1;
- $L_3$ is a monovalent anionic ligand selected from the group consisting of N, P, B when n+o=2, from the group consisting of $NR^1$, $PR^1$, $BR^1$, O and S when n+o=1;
- each X is independently selected from the group consisting of hydrogen, halogen, $NR^2_2$, $R^2$ with $R^2$ equal to $C_1$–$C_{20}$ alkyl, $C_3$–$C_{20}$ cycloalkyl, $C_6$–$C_{20}$ aryl, $C_3$–$C_{20}$ alkenyl, optionally comprising 1 to 5 heteroatoms such as Si, N, P, O, F, Cl, Br.
- q is a number whose value is: 0, 1, 2 or 3, depending on the valence of the metal M, so that q+3 is the valence of M;
- D is a neutral Lewis base, preferably it is selected from the group consisting of linear or cyclic ethers, amines and phosphines; most preferably it is selected from the group consisting of diethyl ether, tetrahydrofurane, aniline, dimethylaniline, triphenylphosphine, n-butylamine;
- p is a number whose value is: 0, 1, 2 or 3.

When m is 1, n is 0 and o is 1, the formula I becomes the following formula Ia:

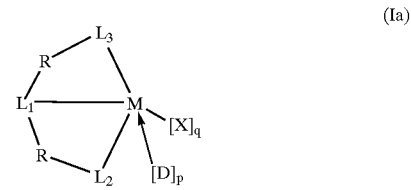

(Ia)

When m is 1, n is 1 and o is 0, the formula I becomes the following formula Ib:

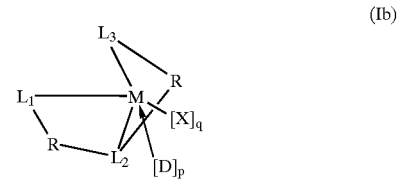

(Ib)

When m is 1, n is 1, o is 0 and $L_2$ is a ligand defied as $L_1$ the formula I becomes the following formula Ic (Ic)

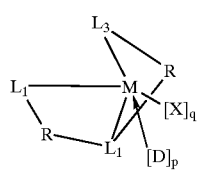

When m, n and o are 1 the formula (I) becomes the following formula Id (Id)

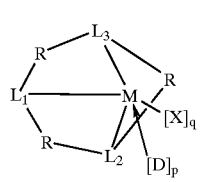

It has been calculated using molecular modeling methods that compounds according to general formula (I) having three ligands rigidly interconnected can have a geometry wherein the bond angles of the metal M are more constrained than the catalyst disclosed in EP 416815. By varying the type of R and the ligands $L_1$, $L_2$ and $L_3$ it is possible to vary the bond angle as well as the steric hindrance on the metal center, influencing in this way Mw, MWD, long chain branching, short chain branching and, in case of $C_3$–$C_{20}$ alpha olefins, the tacticity of the polymer.

A preferred class of compounds belonging to formula Ia is defined by the following formula II:

(II)

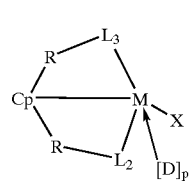

wherein Cp is a cyclopentadienyl or indenyl ring, optionally substituted by one or more $R^1$ groups, M is selected from Ti, Zr and Hf each R is independently selected from $CR^1_2$, $SiR^1_2$, $CR^1_2$—$CR^1_2$, $CR^1_2$—$SiR^1_2$, $SiR^1_2$—$SiR^1_2$, wherein $R^1$ is hydrogen, $C_1$–$C_{20}$ alkyl, $C_3$–$C_{20}$ cycloalkyl, $C_6$–$C_{20}$ aryl, $C_3$–$C_{20}$ alkenyl, optionally comprising 1 to 5 heteroatoms such as Si, N, P, O, F, Cl, Br. Two groups $R^1$ bonded to the same or to adjacent atoms can unite to form a ring.

$L_2$ and $L_3$ are independently selected from the group consisting of $NR^1$, $PR^1$, $BR^1$, O and S;

X is independently selected from the group consisting of hydrogen, halogen, $NR_2$, $R^2$ with $R^2$ equal to $C_1$–$C_{20}$ alkyl, $C_3$–$C_{20}$ cycloalkyl, $C_6$–$C_{20}$ aryl, $C_3$–$C_{20}$ alkenyl, optionally comprising 1 to 5 heteroatoms such as Si, N, P, O, F, Cl, Br.

D is a neutral Lewis base; preferably it is selected from the group consisting of linear or cyclic ethers, amines and phosphines; most preferably it is selected from the group consisting of diethyl ether, tetrahydrofurane, aniline, dimethylaniline, triphenylphosphine, n-butylamine;

p is a number whose value is: 0, 1, 2 or 3.

In one embodiment of the invention, the compounds of formula I are preferably obtained by reacting a compound of formula $MX_{q+3}$ wherein M is a transition metal of groups 3, 4–10, lanthanide or actinide of the periodic table of the elements, X is a monovalent anionic ligand, preferably selected from the group consisting of $N(CH_3)_2$, benzyl, and q is 0, 1, 2, 3 depending on the valence of M, with a compound of formula III (III)

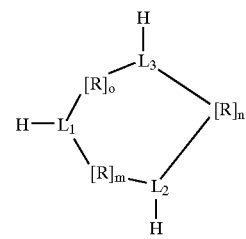

wherein $L_1$ is a group of the cyclopentadienyl type or is isolobal to cyclopentadienyl, preferably a cyclopentadienyl, indenyl or fluorenyl ring, cyclopenteno[b]tiophenyl cyclopenteno[b:b']-dithiophenyl cyclopenteno[b]pyrrolyl, boratabenzene, phospholyl, dihydroindeno[b]indolyl, optionally substituted by one or more $R^1$ groups; most preferably a cyclopentadienyl, indenyl or fluorenyl ring, optionally substituted by one or more $R^1$ groups;

m, n and o are 0 or 1, with the proviso that m+n+o is 2 or 3.

$L_2$ is a ligand of the cyclopentadienyl type or is isolobal to cyclopentadienyl, preferably a cyclopentadienyl, indenyl or fluorenyl ring, cyclopenteno[b]tiophenyl cyclopenteno[b:b']-dithiophenyl cyclopenteno[b]pyrrolyl, boratabenzene, phospholyl, dihydroindeno[b]indolyl, optionally substituted by one or more $R^1$ groups; most preferably a cyclopentadienyl, indenyl or fluorenyl ring, optionally substituted by one or more $R^1$ groups; or it is selected from the group consisting of N, P, B when m+n=2, it is selected from the group consisting of $NR^1$, $PR^1$, $BR^1$, O and S when m+n=1;

$L_3$ is selected from the group consisting of N, P, B when n+o=2, it is selected from the group consisting of $NR^1$, $PR^1$, $BR^1$, O and S when n+o=1;

each R is independently a structural bridge rigidly connecting $L_1$, $L_2$ and $L_3$ and is constituted by 1 to 4 chain atoms selected from carbon, silicon, germanium, oxygen, boron; these atoms can be part of fused rings, aromatics rings or spiro rings;

$R^1$ is hydrogein, $C_1$–$C_{20}$ alkyl, $C_3$–$C_{20}$ cycloalkyl, $C_6$–$C_{20}$ aryl, $C_3$–$C_{20}$ alkenyl, optionally comprising 1 to 5 heteroatoms such as Si, N, P, O, F, Cl, Br.

In order to have complete substitution of three ligands X with $L_1$, $L_2$ and $L_3$ it is in some cases preferable to remove from the reaction medium the compound XH formed during reaction. Depending on the reaction conditions, also the intermediate IV can be formed.

(IV)

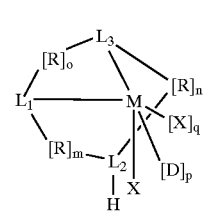

The intermediate IV is then further reacted with a compound of formula II with X equal to benzyl, to produce the compound of formula I.

Alternatively, it is possible to react one mole of compound III with three moles of a strong base such as butyllithium, NaH, KH, etc. The trianion is then treated with $MX_{q+3}$, optionally complexed with a Lewis base D, to obtain the compound of formula I, with X equal to halogen, preferably Cl.

Another suitable process for the preparation of compounds of formula I is to treat the compound (III) with $NR_3$ in the presence of $MX_{q+3}$.

The organometallic compounds of the present invention are useful as catalyst components for polymerizing olefins, preferably alpha-olefins in combination with a co-catalyst. Illustrative but non-limiting examples of co-catalysts are: aluminoxanes (methylalumninoxane (MAO), modified methylaluminoxane (MMAO), etc.), combinations of alkylaluminiums (such as trimethylaluminium, triethylaluminium, tributylaluminium, etc.) and boron Lewis acids (such as trifluoroborane, tris-pentafluorophenylborane, tris[3,5-bis(trifluoromethyl)phenyl]borane, etc.), and compounds of formula $J^+K^-$ wherein $J^+$ is able to react irreversibly with a group X in formula I and $K^-$ is an anion which is able to stabilize the catalytic species which originates from the reaction of the two compounds and which is sufficiently labile to be able to be removed from an olefinic substrate (triphenylcarbenium tetrakis(pentafluorophenyl) borate, dimethylanilinium tetrakis(pentafluorophenyl) borate, $HBF_4$, $AgBF_4$, $AgPF_6$, $AgSbF_6$, silver tetrakis[3,5-bis(trifluoromethyl)phenyl]borate, sodium tetrakis[3,5-bis (trifluoromethyl)phenyl]borate, etc.).

The catalyst component of the present invention, i.e. organometallic compound complex of formula I, can be used either as homogeneous catalyst or heterogeneous. In the latter case, it is preferred to use a organometallic compound (I) wherein at least one L group (selected from $L_1$, $L_2$ and $L_3$) and/or one R group contains a functional group capable or forming a covalent bond with the support. Suitable functional groups are: $-O-SiR^2_3$, $-SiR^2nX_{3-n}$, $SiR^2_n(OR^2)_{3-n}$, $-OH$. This type of compounds are disclosed in EP 839 836, EP 757 992, EP 293 815, EP 953 580, EP 953 381 and WO 99/52949. The preferred functional group is $-O-SiR^2_3$ and is preferably linked to the organometallic compound through a divalent radical comprising from 1 to 20 carbon atoms and from 0 to 5 chain atoms different from carbon and preferably selected from silicon, oxygen, sulfur, boron, phosphorus, nitrogen.

The divalent radical joins the group $-O-SiR^2_3$ either to the Cp ring or to one of the atoms of R or to the anionic ligand, as described in EP 839 836.

As supporting material, any type of inorganic oxides are used, for example inorganic oxides such as: silica, alumina, silica-alumina, aluminum phosphates and mixtures thereof, obtaining supported catalysts with contents in transition metals between 0.01 and 4% by weight, preferably between 0.1 and 1%. A particularly preferred support is silica calcined at a temperature between 600° C. and 800° C. and also MAO modified silica.

For the polymerization in solution, the cocatalyst is mixed with a solution of a organometallic compound of formula I and a supplementary quantity of it optionally is added to the solution; or the catalyst can directly be added to the polymerization medium, which contains the cocatalyst.

For the polymerization in suspension, the cocatalyst is previously mixed with the supported solid catalyst or it is added to the polymerization medium before the supported catalyst, or both operations are sequentially realized.

The most proper polymerization procedure can change according to the chosen type of polymerization process (solution, suspension, slurry or gas phase).

The process consists in putting in contact the monomer, or, in certain cases, the monomer and the comonomer, with a catalytic composition according to the present invention, that includes at least one organometallic compound of formulas I and/or II, at a proper temperature and pressure.

$C_2-C_{12}$ alpha-olefins, such as ethylene, propylene, 1-butene, 1-hexene, 1-octene, 4-methyl-1-pentene, styrene, divinylbenzene are used as monomer. In case ethylene is used as monomer, it can be either homopolymerized, or copolymerized in the presence of at least one comonomer selected from propylene, 1-butene, 1-hexene, 1-octene, 4-methyl-1-pentene. These comonomers are used in proportions from 0.1 to 70% by weight of the total of the monomers. In the case of homopolymerization of ethylene the density of polymers ranges between 0.950 and 0.970 kg/cm³ in the case of copolymerization of ethylene the density is as low as 0.880 kg/cm³.

In the particular case of the polymerization technique known as suspension or slurry process, the used temperature will be between 30° and 110° C., the same which is typically used in gas phase, while for the solution process the usual temperature will be between 120° and 250° C.

Preferred compounds of formula I are:

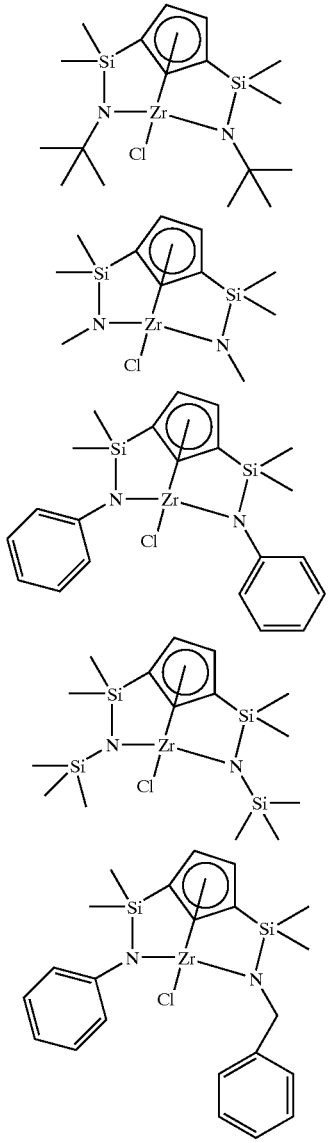

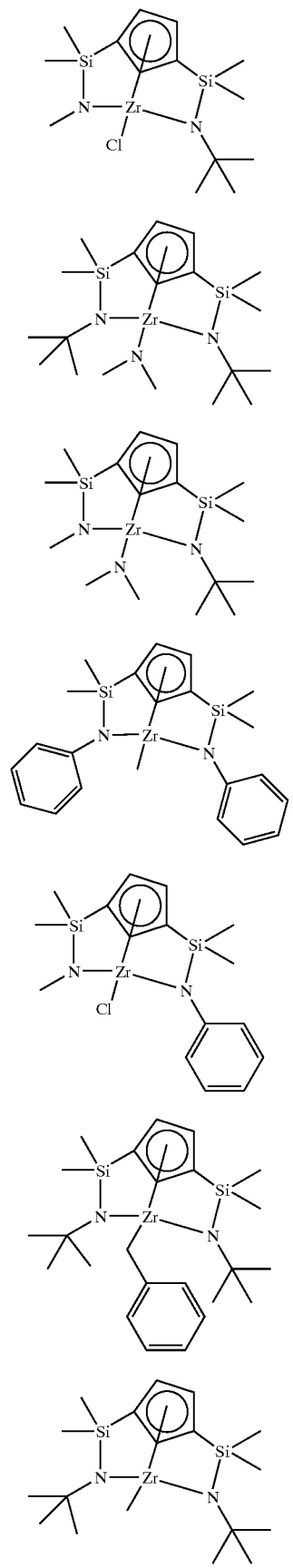

-continued
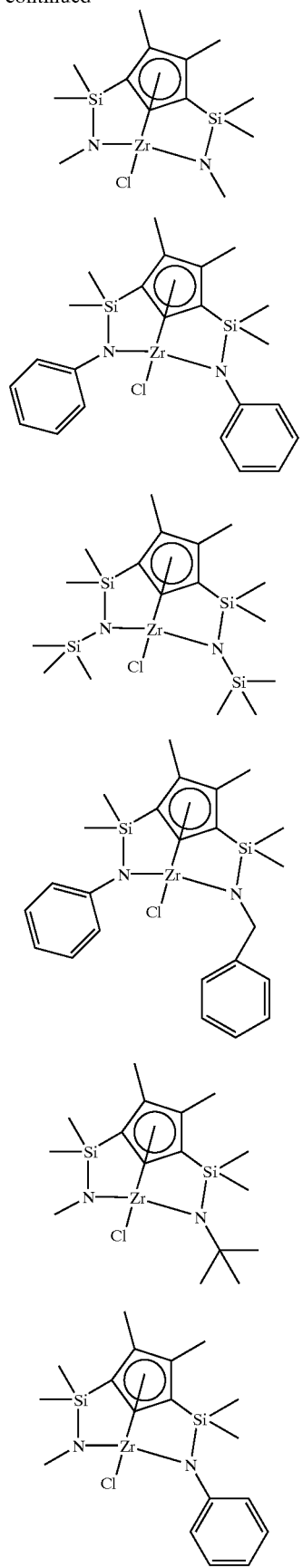
-continued
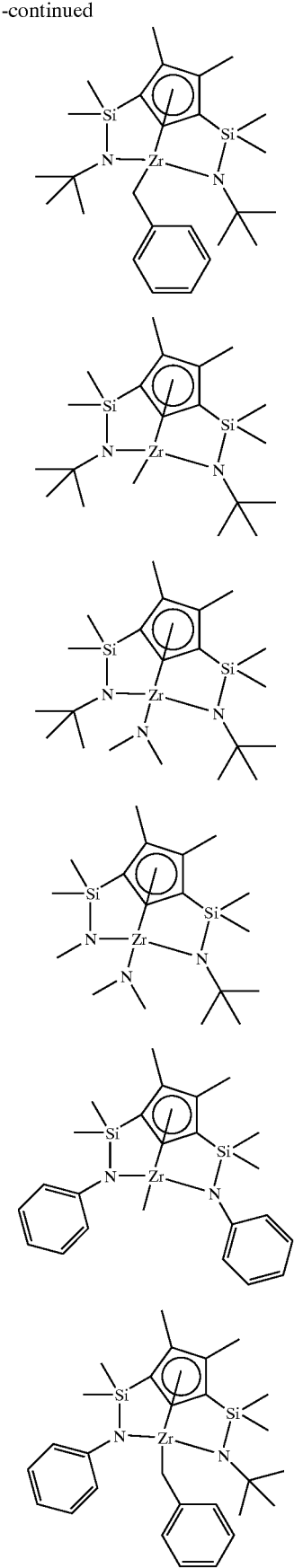

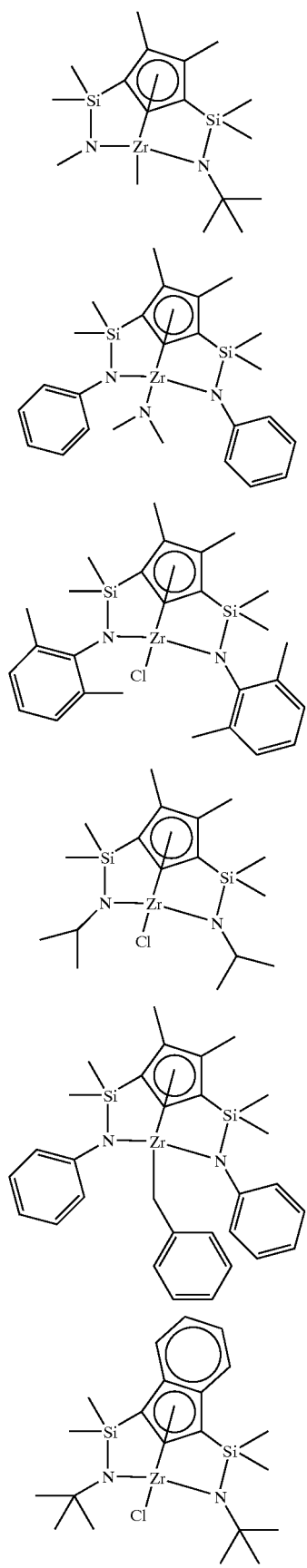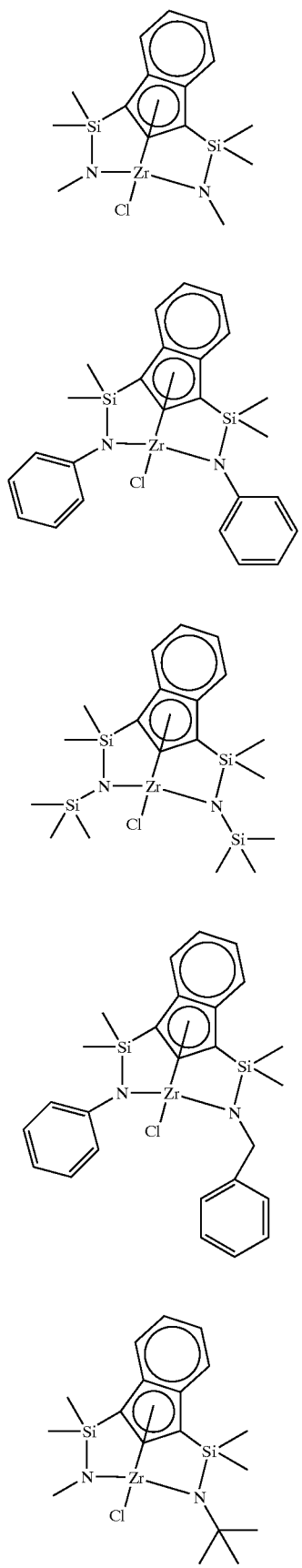

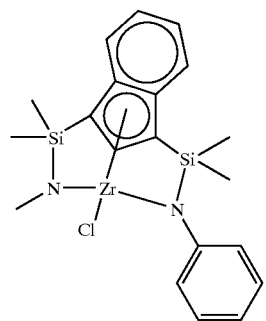
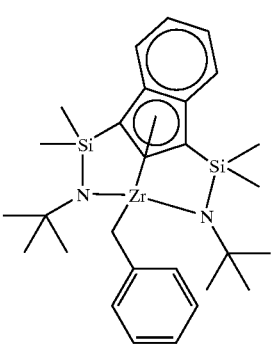
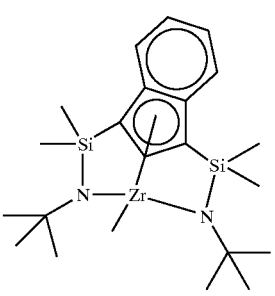
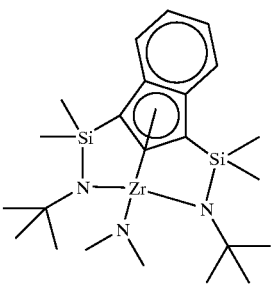
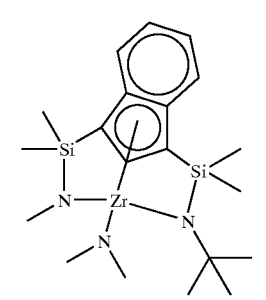
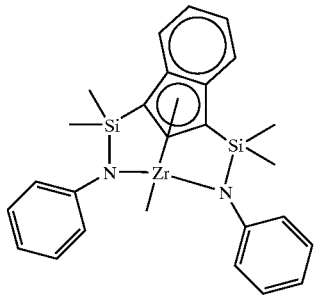
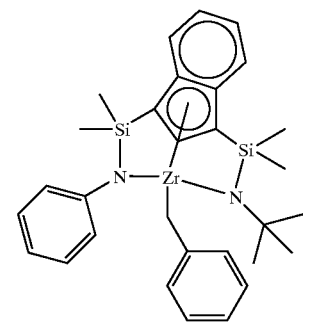
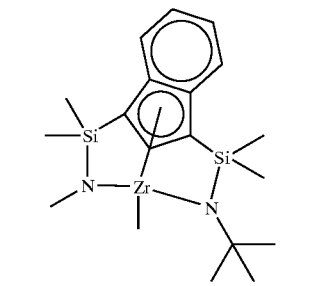
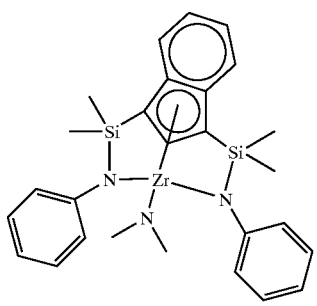
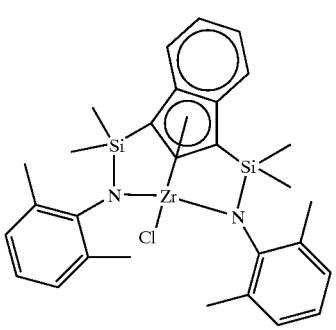

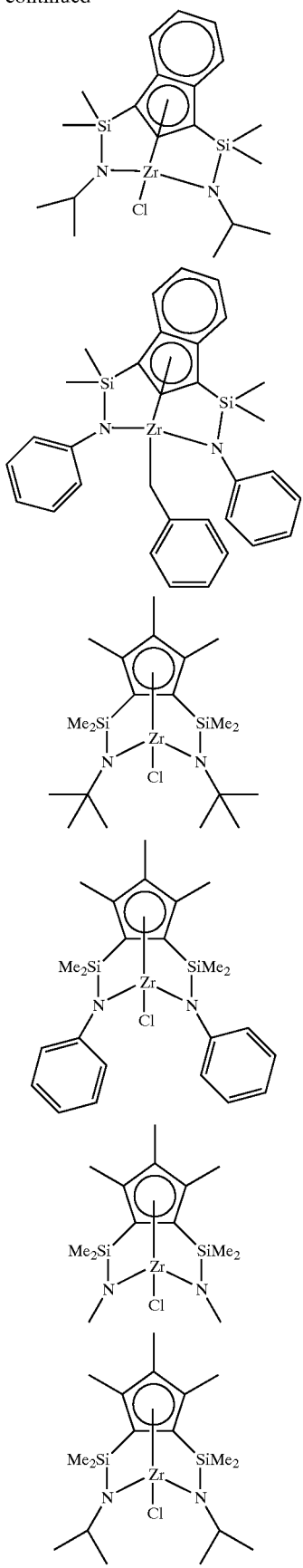
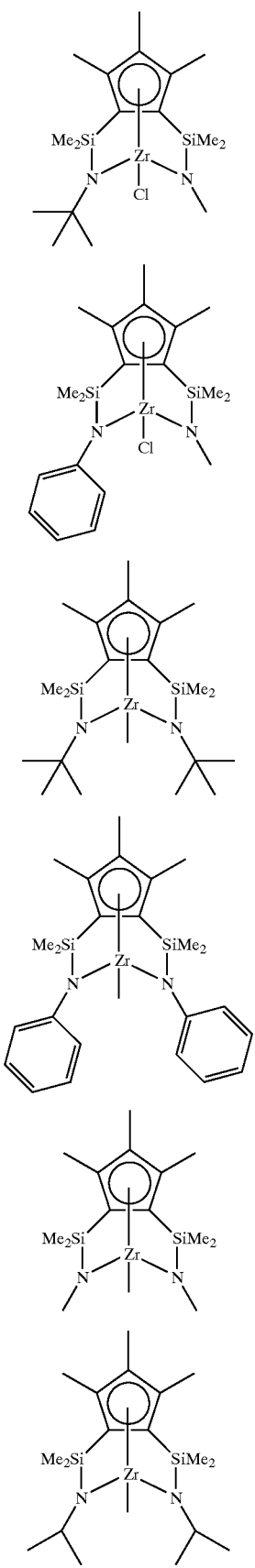

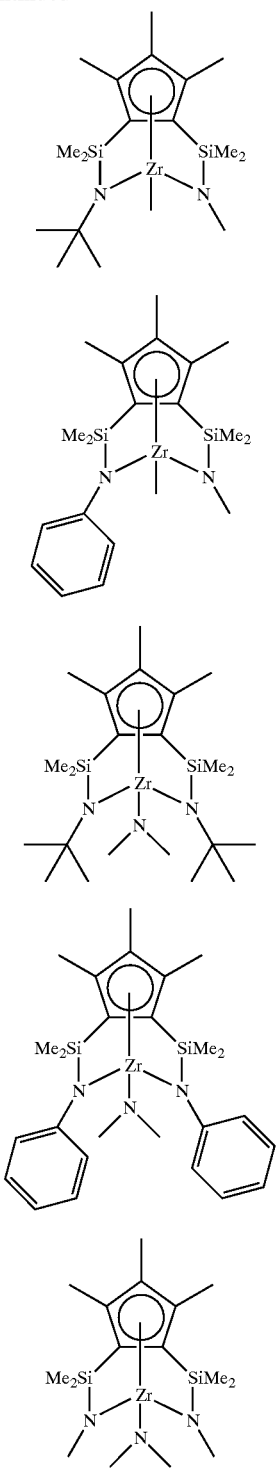

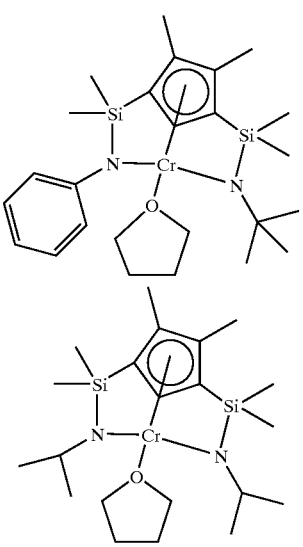

Further examples of compounds belonging to the invention are obtained by substituting zirconium in the above listed compounds with titanium or hafnium.

These compounds can be synthesized starting from the corresponding compound of formula III, which can be synthesized using methods similar to those described in the experimental part starting from the appropriate cyclopentadienyl derivative, $Me_2SiCl_2$ and amine derivatives.

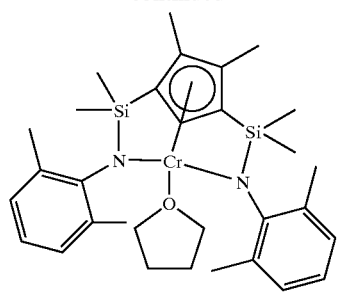
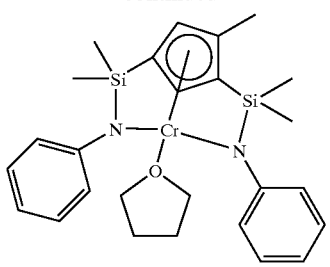
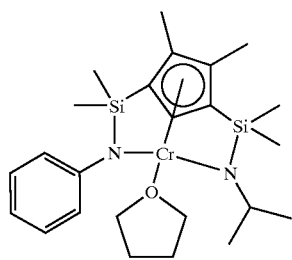
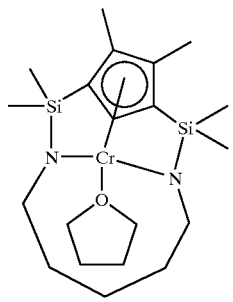
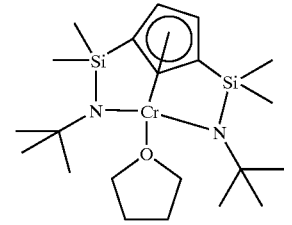
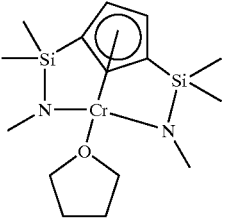
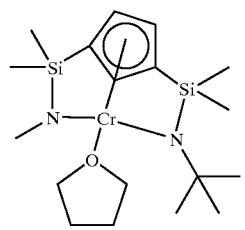
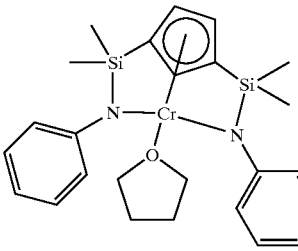
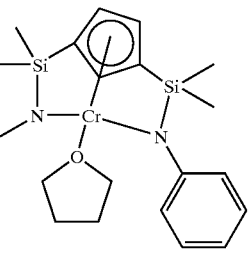
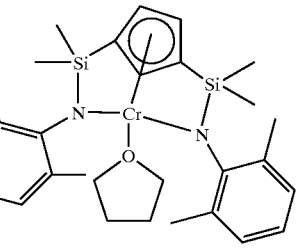
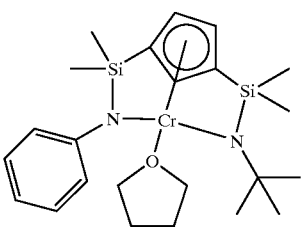
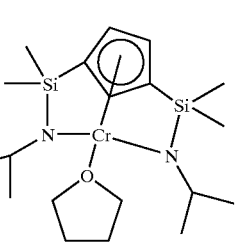
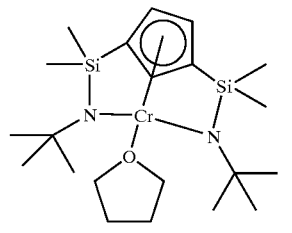
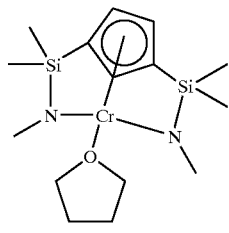
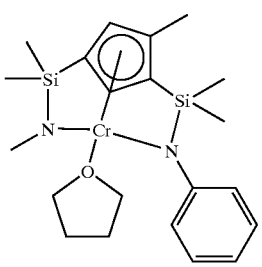
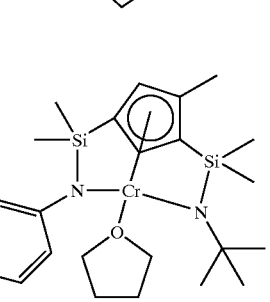

-continued

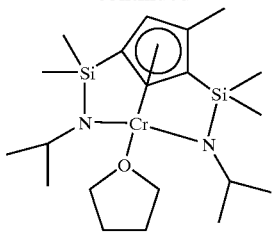

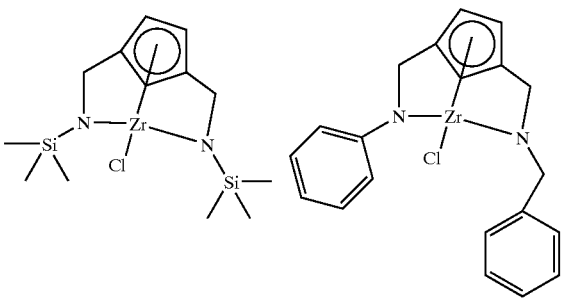

Further examples include compounds wherein the tetrahydrofairane ligand in the previous examples shown in b) is replaced by pyrydine.

These compounds can be synthesized starting from the corresponding compound of formula III, which can be synthesized using methods similar to those described in the experimental part starting from the appropriate cyclopentadienyl derivative, $Me_2SiCl_2$ and amine derivatives. The corresponding compound of formula I can be synthesized using similar methods to those described in the experimental part starting from the compound of formula III and the appropriate chromium III complex, such as $CrCl_3(THF)_2$.

c)

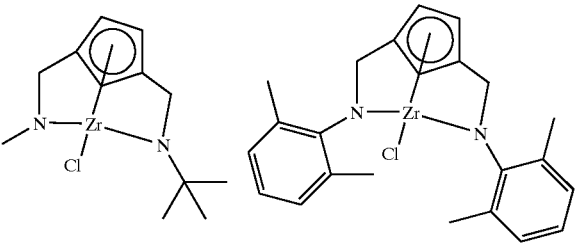

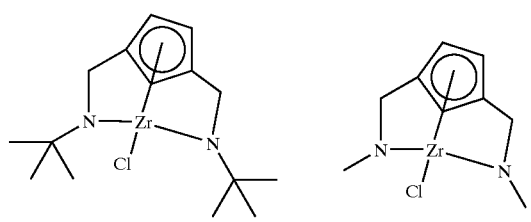

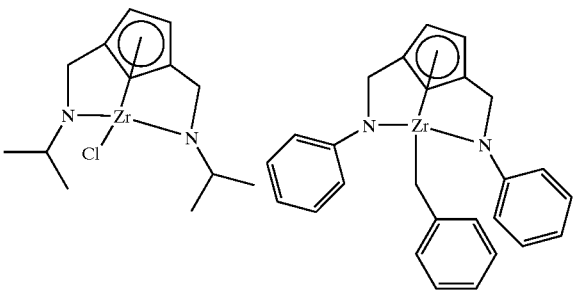

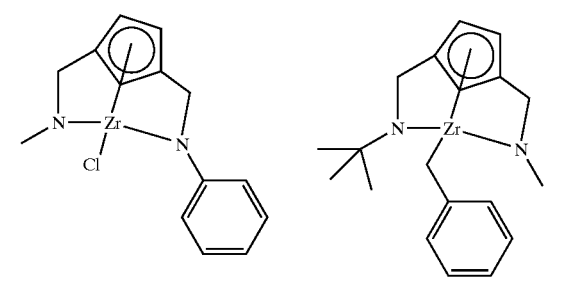

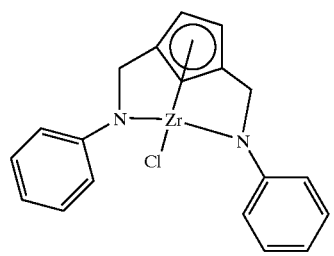

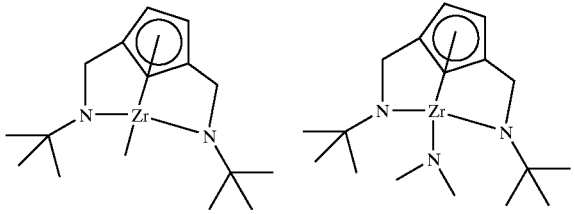

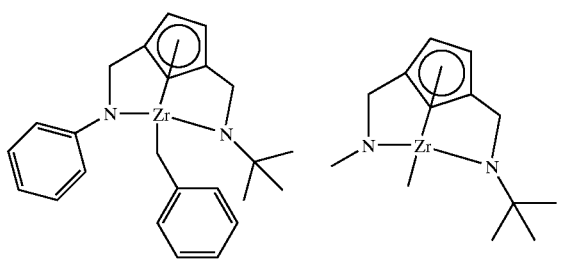

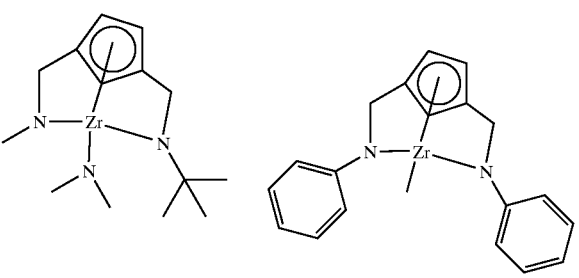

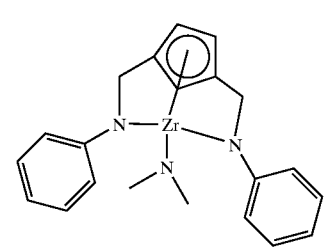

Further examples include compounds wherein the zirconium atom in the previous examples shown in c) is replaced by Ti, Hf These compounds can be synthesized starting from the corresponding compound of formula III, which can be synthesized using methods similar to those described in Organometallics 1997, 16, 2891; Topics in Catalysis 7, 1999, 37; Eur. J. Inor. Chem. 1998, 1153.
d)
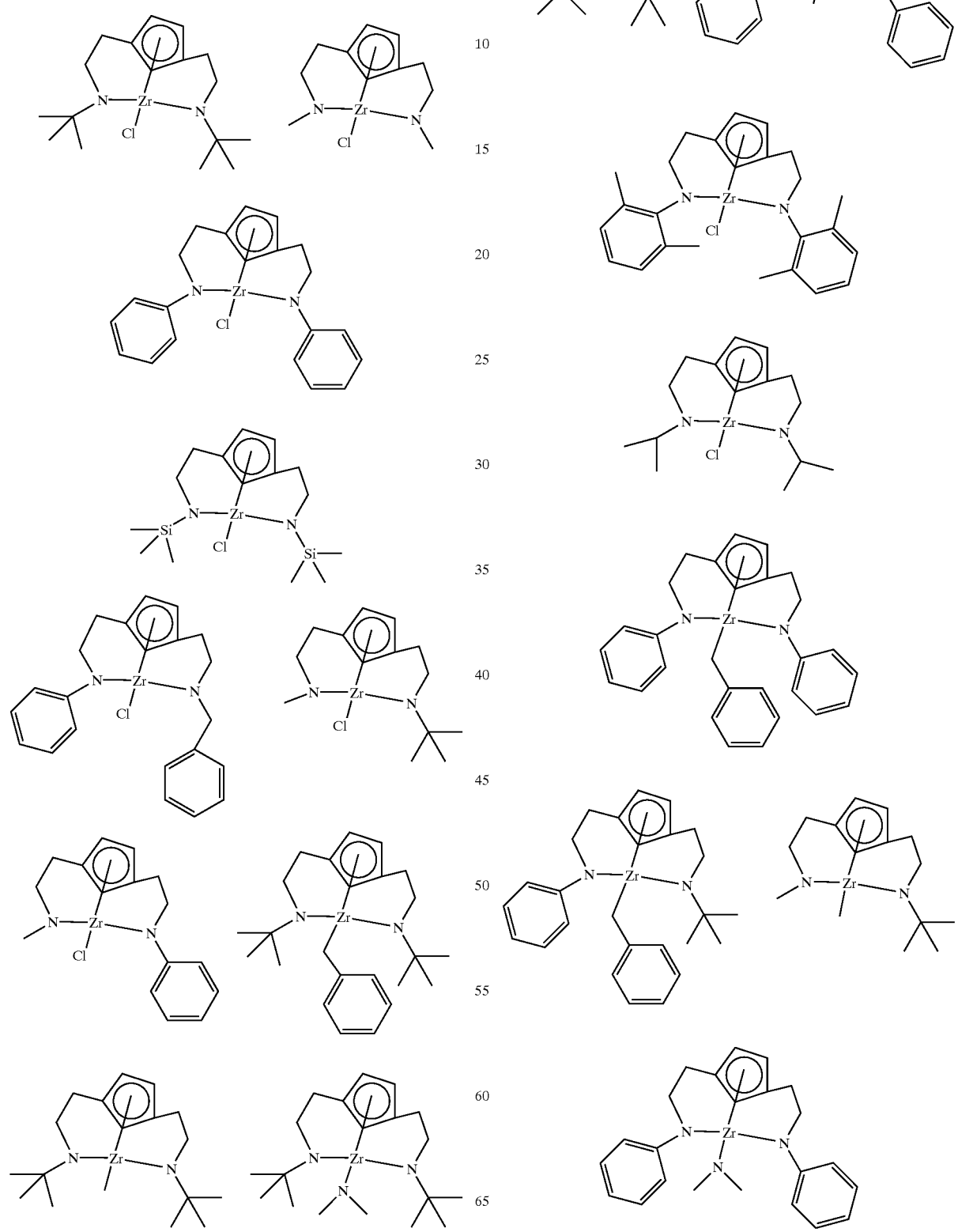

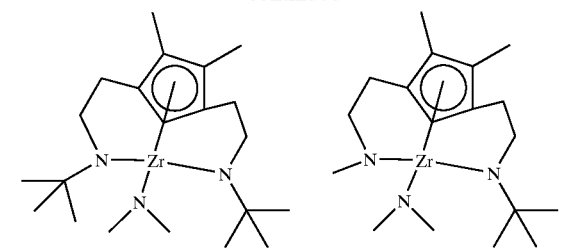
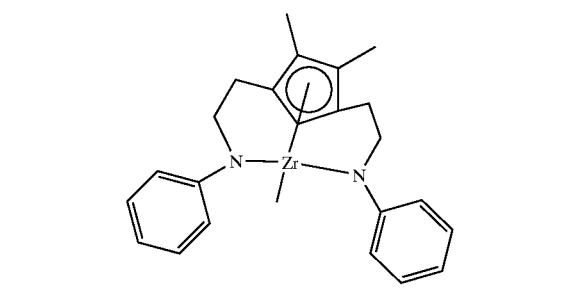
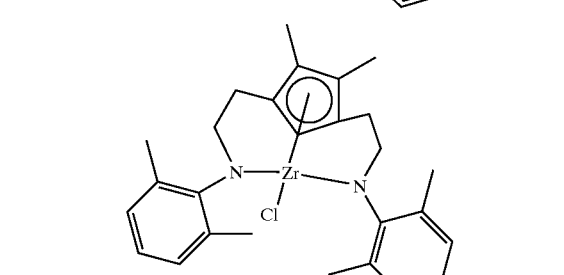
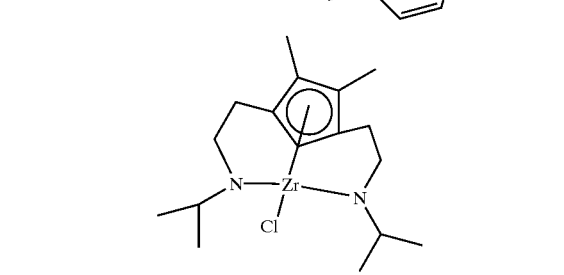
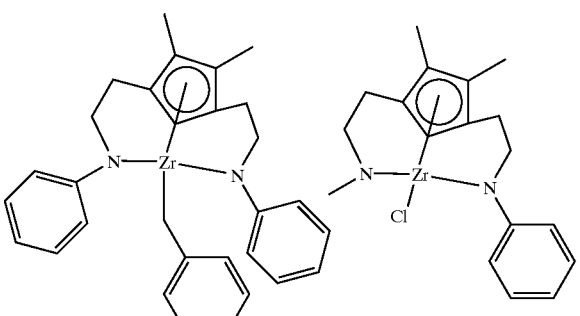
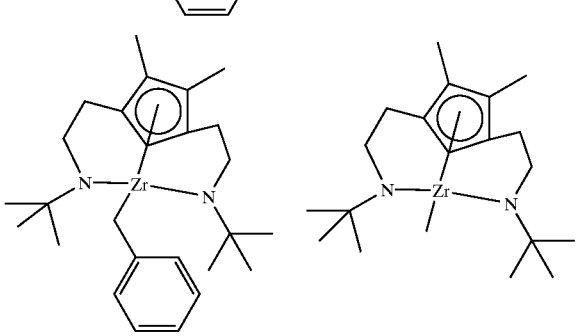
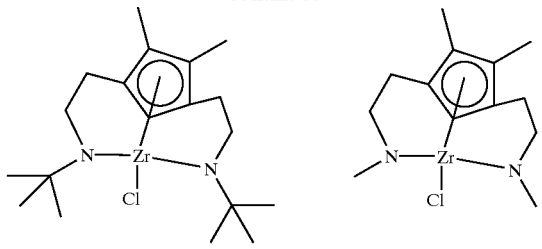
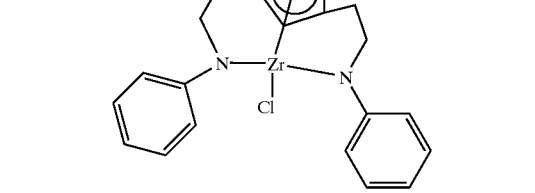
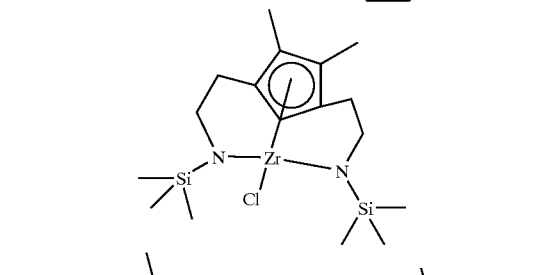
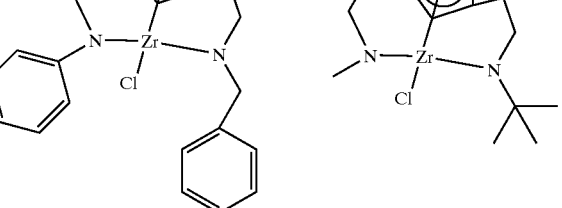
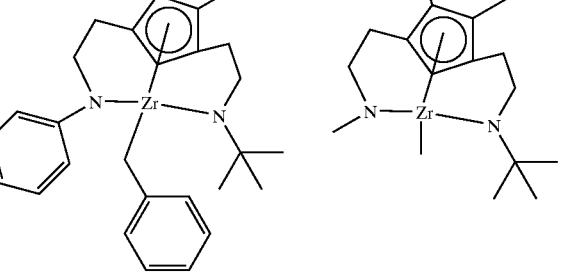
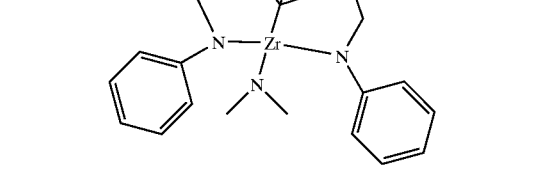

Further examples include compounds wherein the zirconium atom in the previous examples shown in d) is replaced by Ti, Hf
These compounds can be synthesized starting from the corresponding compound of formula III, which can be synthesized using methods similar to those described in Organometallics 19,2000, 4071.
e)
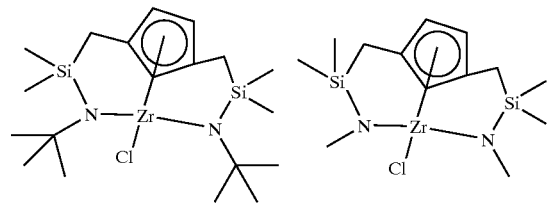
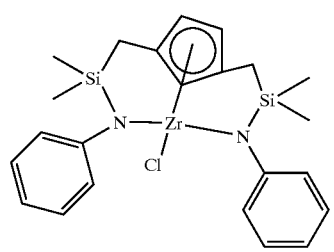
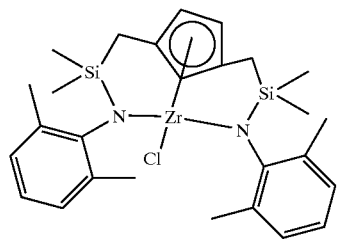
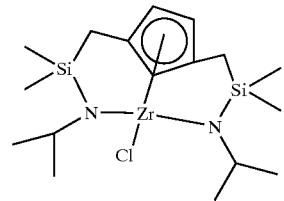
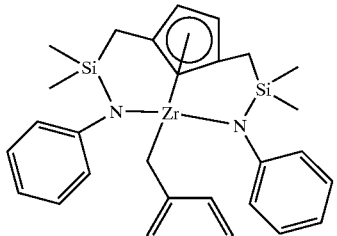
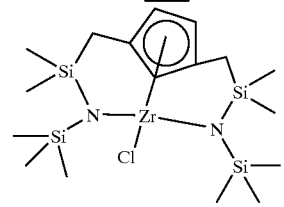
-continued
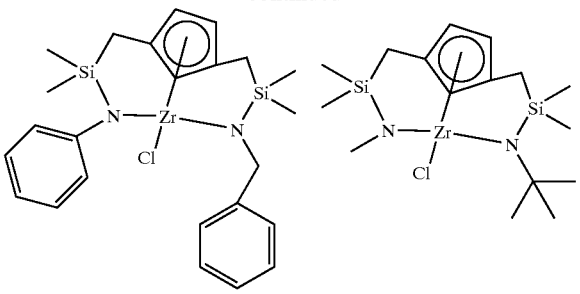
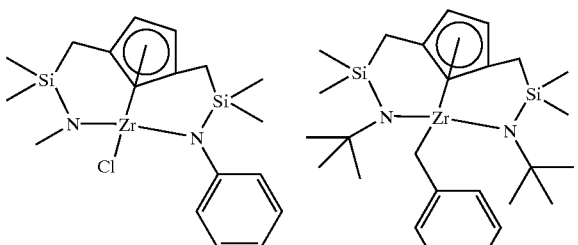
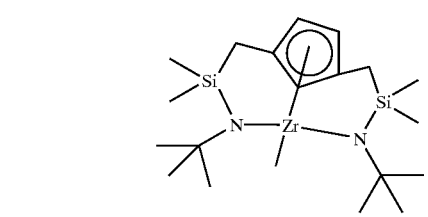
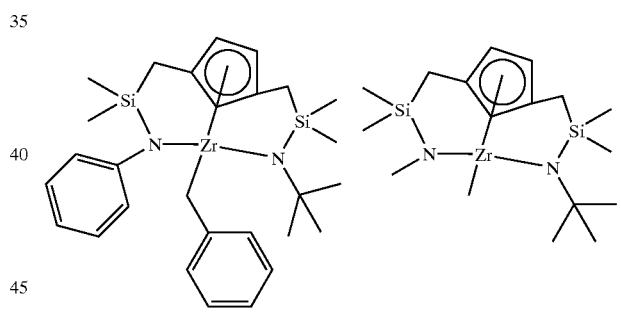
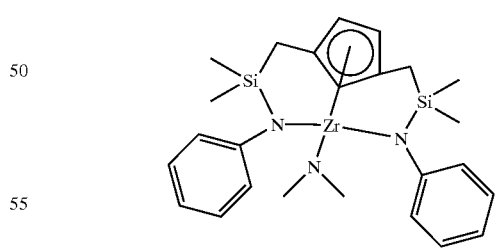
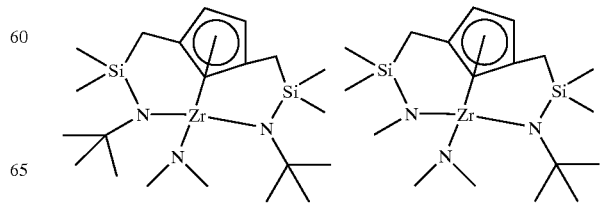

-continued
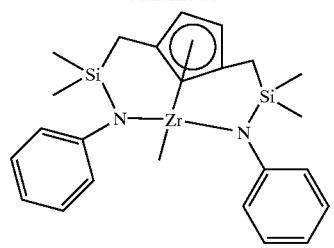
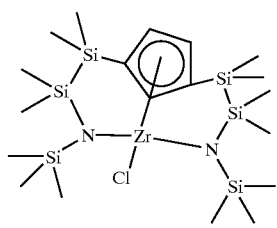
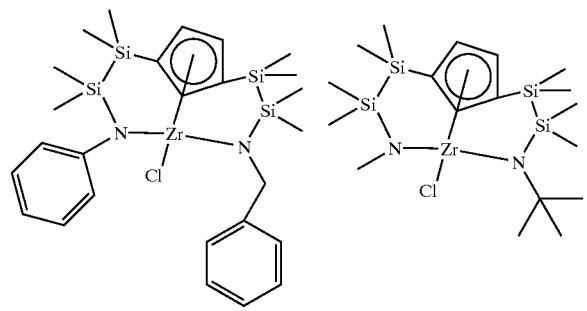
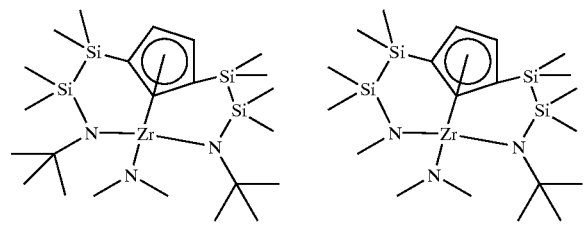
-continued
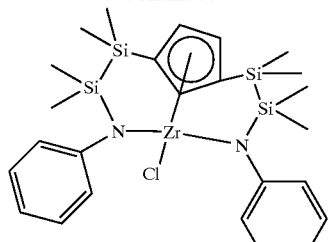
Further examples include compounds wherein the zirconium atom in the previous examples shown in e) is replaced by Ti, Hf
These compounds can be synthesized starting from the corresponding compound of formula III, which can be synthesized using methods similar to those described in EP0839834, EP416185.
f)
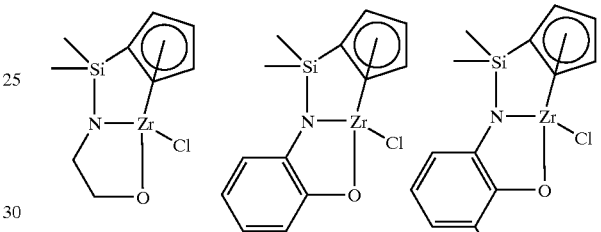
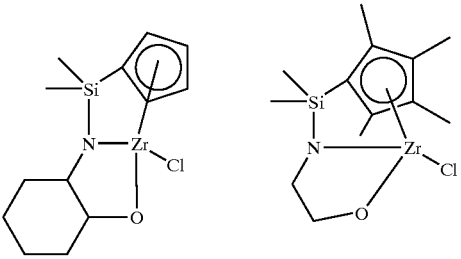
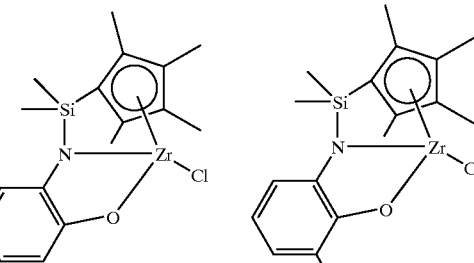
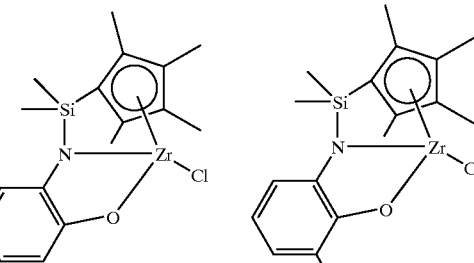
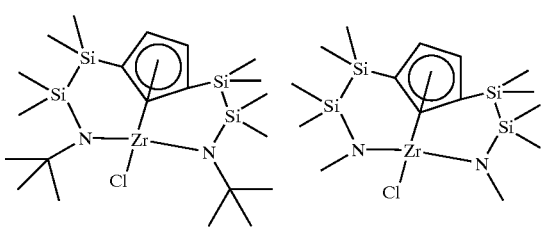
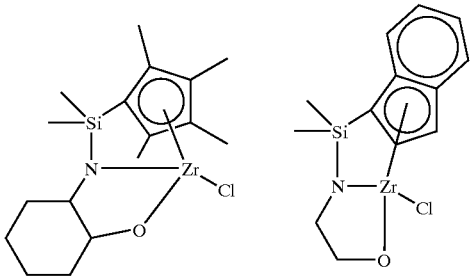

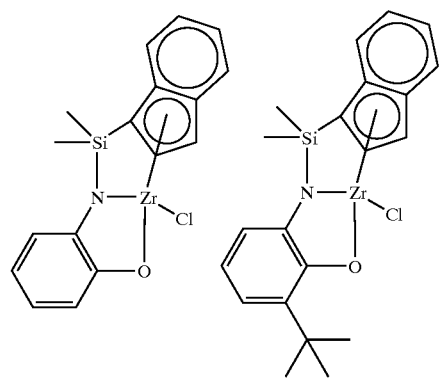
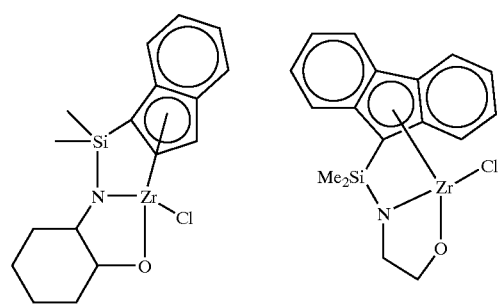
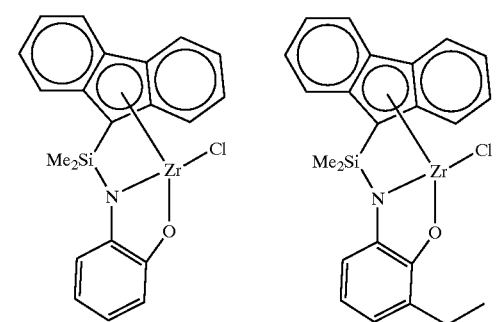
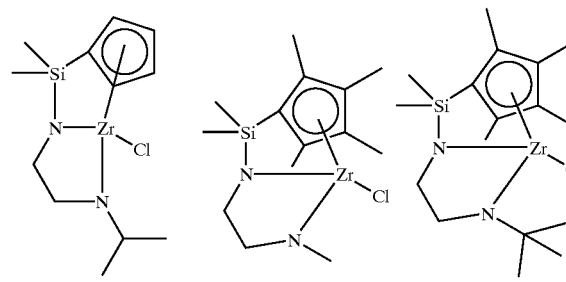
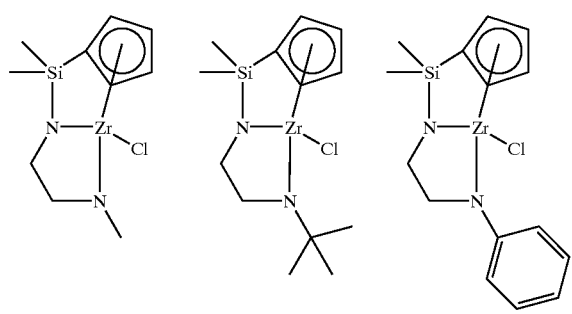
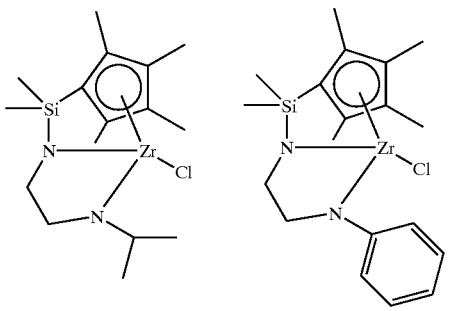
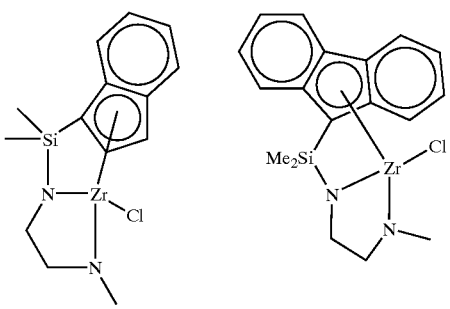
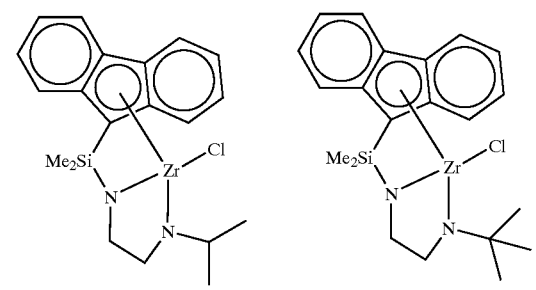
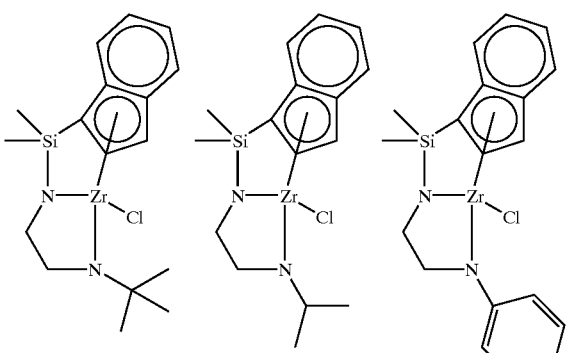
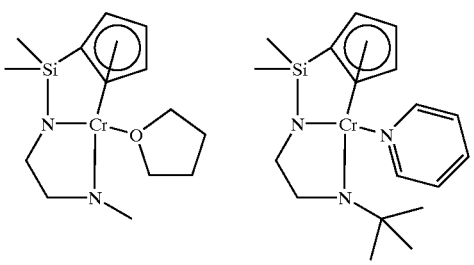

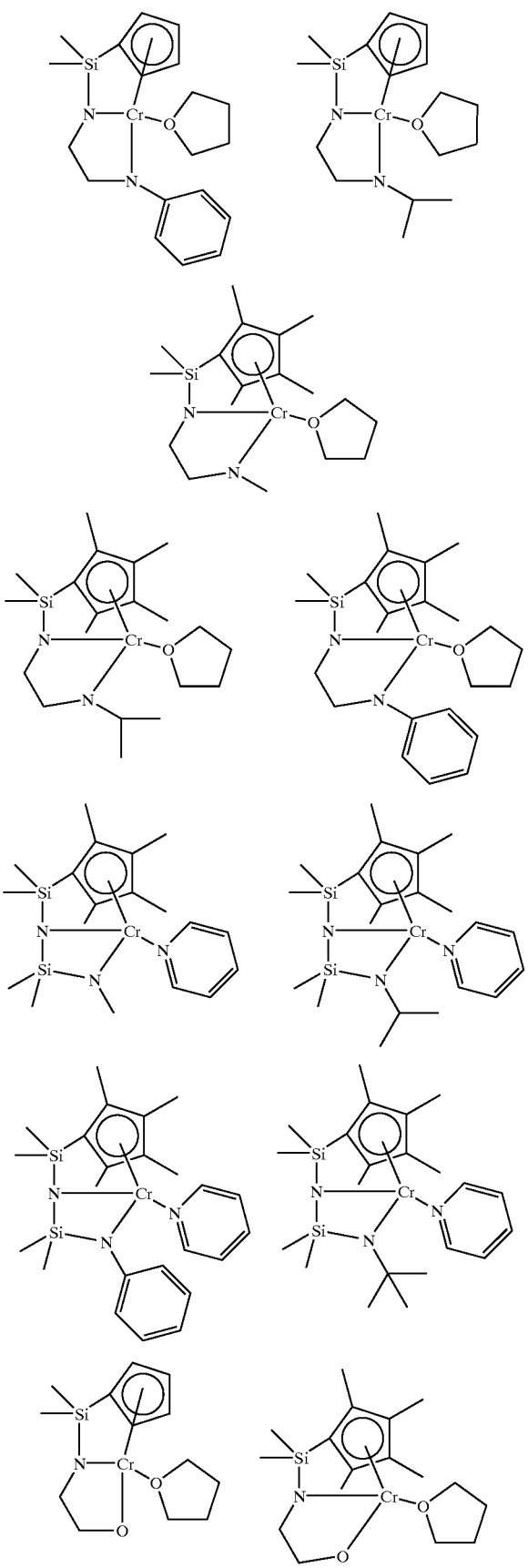

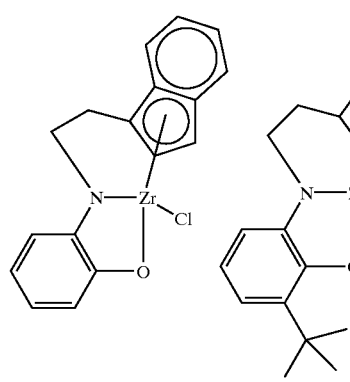
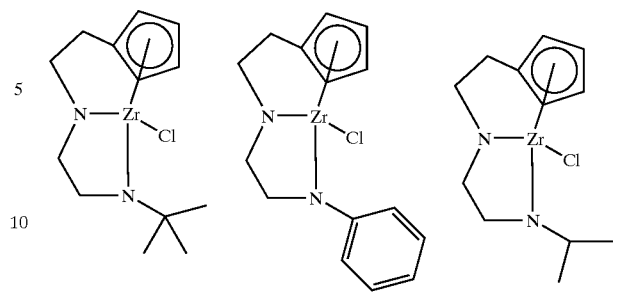
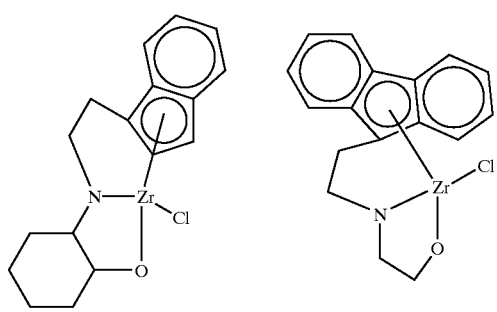
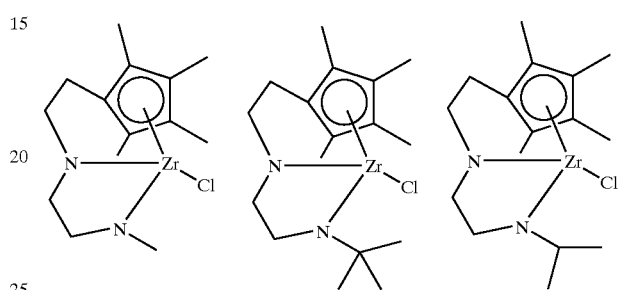
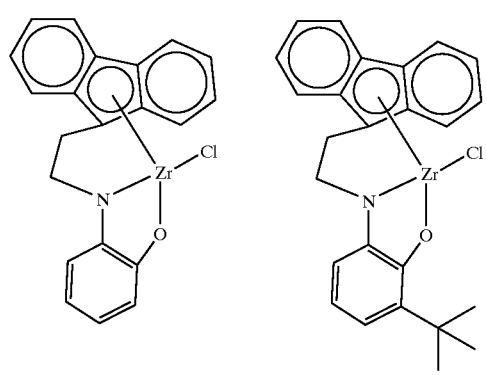
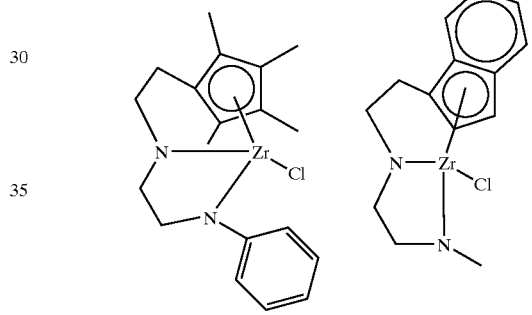
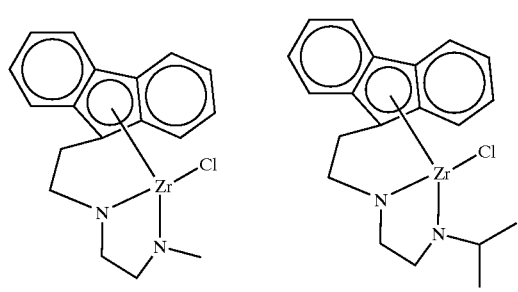
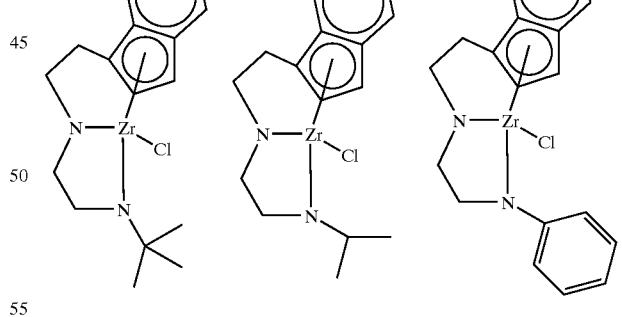
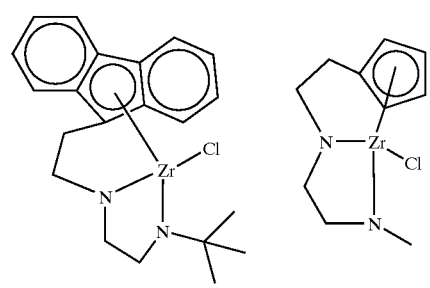

Further examples include compounds wherein the zirconium atom in the previous examples shown in f) is replaced by Ti, Hf The previous compounds can be synthesized using similar methods described in the literature. The corresponding compound of formula III can be synthesized using similar methods to those described in J. Organomet. Chem. 558, 1998, 139; Chem. Ber. 1996, 129, 275 starting from the appropriate cycolpentadienyl derivative and the appropriate protected amine or alcohol followed by deprotection.

g)
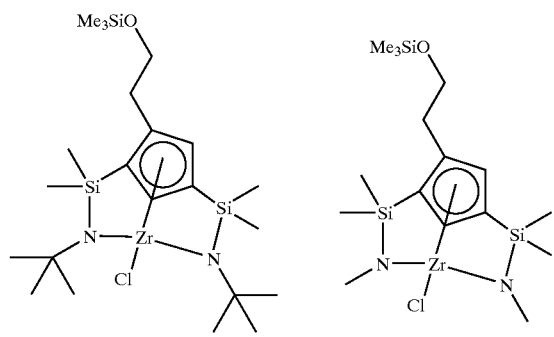
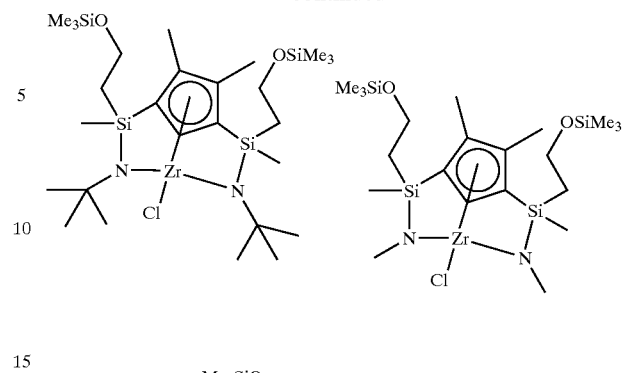
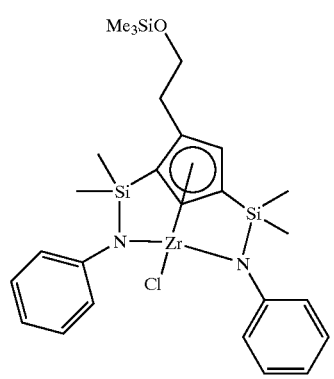
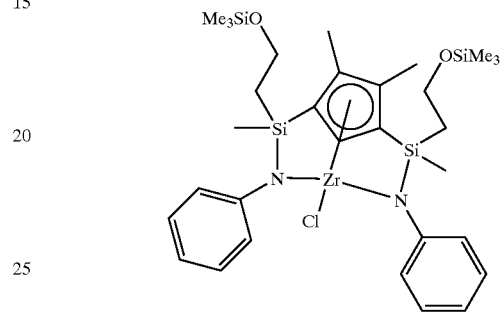
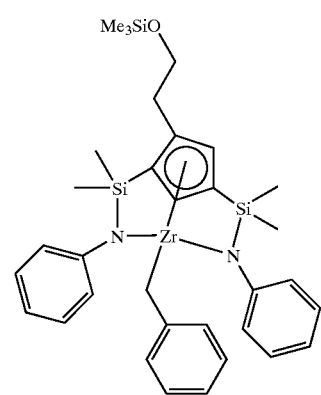
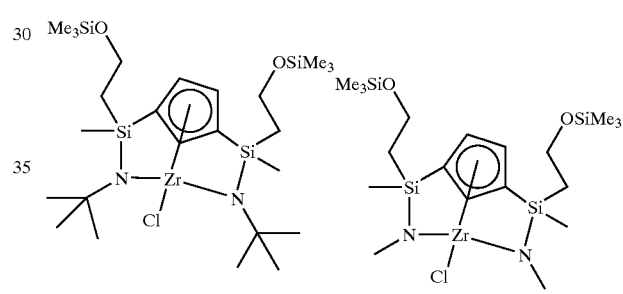
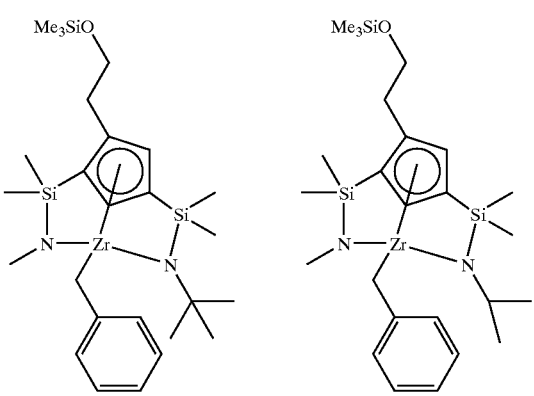
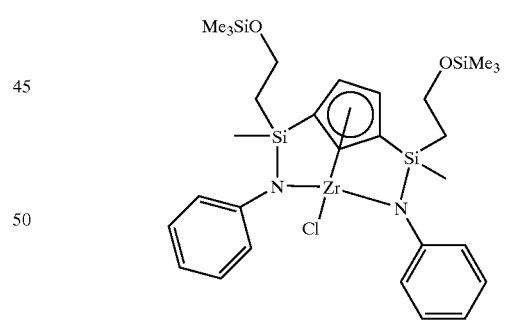
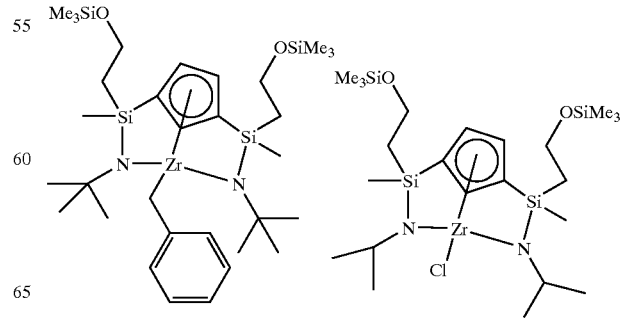

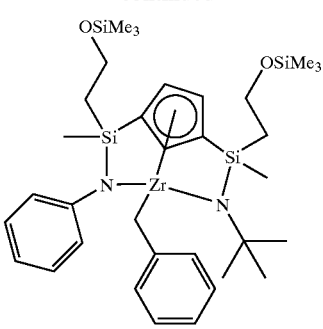
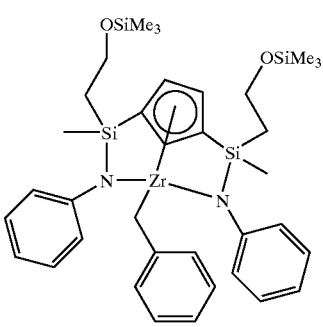
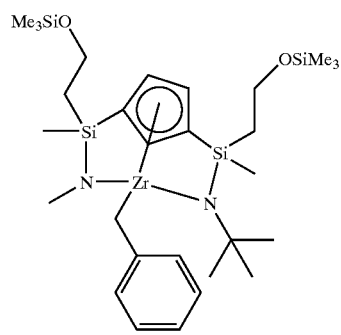
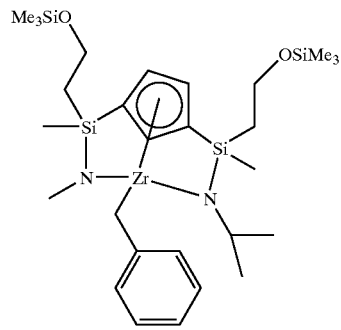
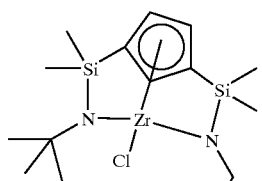
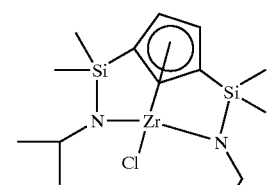
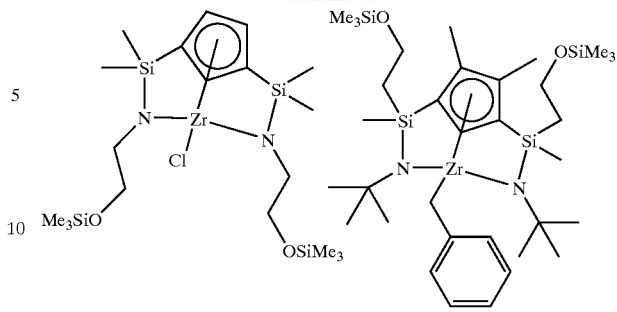
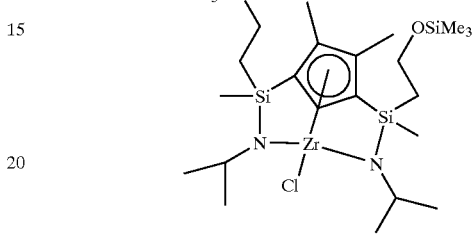
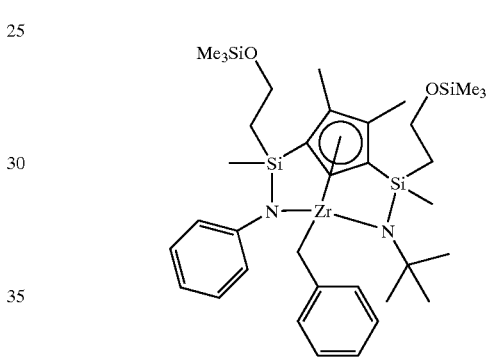
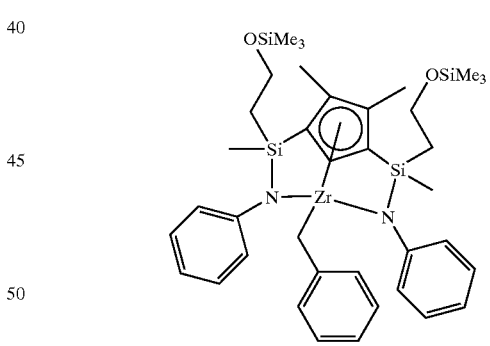
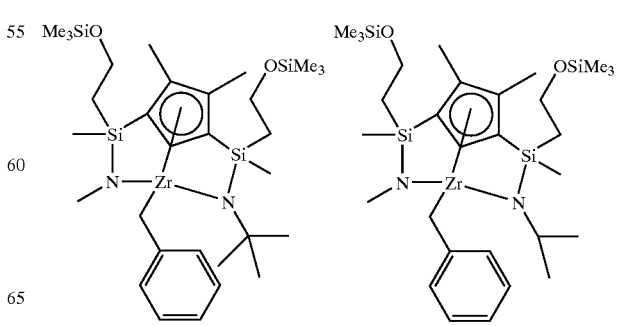

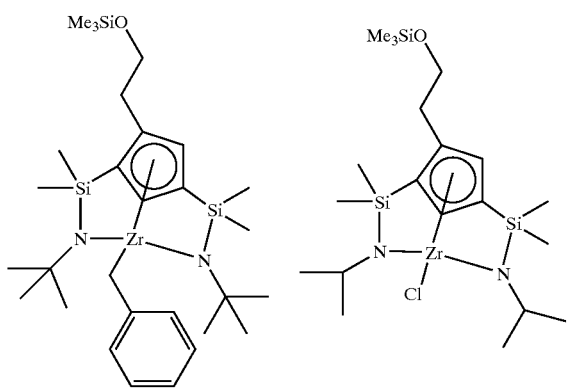

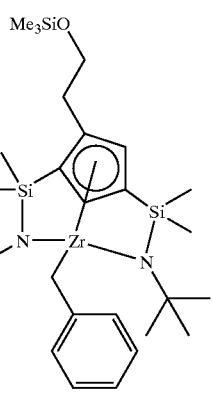

Further examples include compounds wherein the zirconium atom in the previous examples shown in g) is replaced by Ti, Hf.

These compounds can be synthesized starting from the corresponding compound of formula III, which can be synthesized using methods similar to those described in EP953581, EP839836 and European patent application number 99500196.3.

h)

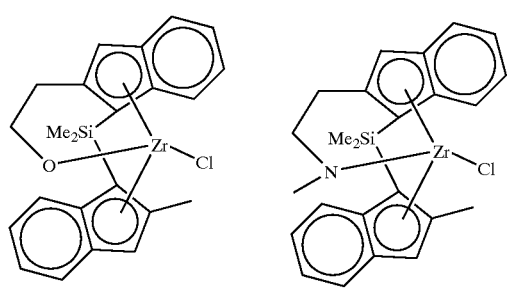

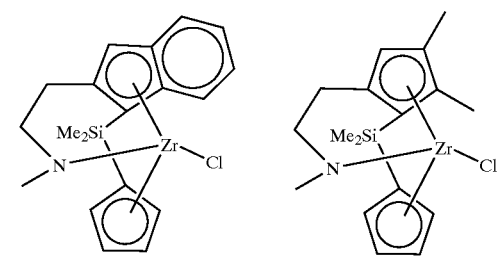

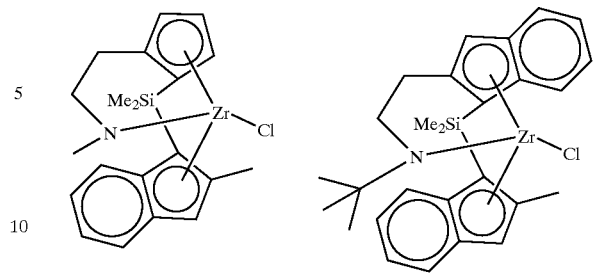

Further examples include compounds wherein the zirconium atom in the previous examples shown in h) is replaced by Ti, Hf.

These compounds can be synthesized starting from the corresponding compound of formula III, which can be synthesized using methods similar to those described in Organometallics 1999, 18, 4147.

Experimental

Synthesis of Compounds 1–9

All manipulations were performed under an inert atmosphere of argon or nitrogen using syringes or cannulae through Subaseals in Schlenk tubes using high vacuum line techniques or a glovebox. Solvents were dried and distilled under nitrogen: diethyl ether and tetrahydrofurane from sodium benzophenone ketyl; benzene and toluene from sodium and hexane from sodium/potassium alloy. Compound $C_5H_4$-1,1-$(SiMe_2Cl)_2$ was prepared according to Organometallics, 1985, 4, 2206. The $^1H$ and $^{13}C$ NMR spectra were recorded at 299.95 and 75.43 MHz respectively on a Varian Unity 300 spectrometer; chemical shifts, in ppm, are positive downfield with respect external $SiMe_4$; coupling constants are in Hz. IR spectra were recorded in Nujol mulls for solids on a Perkin-Elmer 583 spectrophotometer. C and H analyses were performed with a Perkin-Elmer 240-B microanalyzer.

Preparation of $C_5H_4[SiMe_2(NH^tBU)]_2$ (1)

A solution of 2.1 equivalents of $LiNH^tBu$ in THF was added at 0° C. to a solution of 1 equivalent of $C_5H_4$-1,1-$(SiMe_2Cl)_2$ in THF and the mixture was stirred for 12 h. The volatiles were removed under vacuum and the residue extracted with hexane to give (1) as a yellow oil in 90% yield.

Preparation of $[Zr\{\eta^5-C_5H_3[SiMe_2(NHBu^t)][SiMe_2(\eta^1-NBu^t)\}(NMe_2)_2]$ (2)

A solution of $Zr(NMe_2)_4$ (3.37 g, 12.6 mmol) in THF (70 mL) was cooled to 0° C. and 1 (4.09 g, 12.6 mmol) was added by syringe. The resulting yellow solution was refluxed during 5 h. When the gas stopped the solvent was removed under vacuum and the residue was extracted into pentane (70 mL). After filtration and removal of the solvent complex 2 was isolated as a light brown oil. (6.19 g, 12.3 mmol, 98%). $^1H$-NMR (300 MHz, $C_6D_6$, 20° C., TMS): δ0.35 (s, 3H, $SiMe_2NH^tBu$), 0.42 (s, 3H, $SiMe_2NH^tBu$), 0.57 (s, 3H, $SiMe_2N^tBu$), 0.59 (s, 3H, $SiMe_2N^tBu$), 0.85 (s, 1H, $NH^tBu$), 1.11 (s, 9H, $NH^tBu$), 1.27 (s, 9H, $N^tBu$), 2.81 (s, 6H, $NMe_2$), 2.82 (s, 6H, $NMe_2$), 6.39 (m, 1H, $C_5H_3$), 6.47 (m, 1H, $C_5H_3$), 6.69 (m, 1H, $C_5H_3$); $^{13}C$-NMR (300 MHz, $C_6D_6$, 20° C., TMS): δ2.3 ($SiMe_2$), 2.7 ($SiMe_2$), 2.8 ($SiMe_2$), 3.0 ($SiMe_2$), 33.9 ($NH^tBu$), 34.9 ($N^tBu$), 44.2 ($NMe_2$), 44.5 ($NMe_2$), 49.6 ($NH^tBu_{ipso}$), 56.6 ($N^tBu_{ipso}$), 111.4 ($C_5H_{3ipso}$), 122.6 ($C_5H_3$), 122.9 ($C_5H_3$); 124.6 ($C_5H_3$), 126.7 ($C_5H_3$). IR (Nujol) ν=3384 cm$^{-1}$ (N—H). Anal. Found: C, 49.73; H, 9.05; N, 11.45. Calc.: C, 50.24; H, 9.24; N, 11.16.

Preparation of [Zr{$\eta^5$-C$_5$H$_3$-1,3-[SiMe$_2$($\eta^1$-NBu$^t$)]$_2$}(NMe$_2$)] (3)

When a 1/1 molar ratio of [Zr{$\eta^5$-C$_5$H$_3$-1,3-[SiMe$_2$($\eta^1$-NBu$^t$)]$_2$}(CH$_2$Ph)] (see preparation (5) below) and the diamido 2 derivatives in C$_6$D$_6$ was heated for 12 h to 120° C. in a sealed NMR tube, the amido compound 3 was formed as the unique reaction product and identified by NMR spectroscopy. $^1$H-NMR (300 MHz, C$_6$D$_6$, 20° C., TMS): δ0.51 (s, 6H, SiMe$_2$), 0.55 (s, 6H, SiMe$_2$), 1.31 (s, 18H, N$^t$Bu), 2.77 (s, 6H, NMe$_2$), 6.34 (m, 1H, C$_5$H$_3$), 6.78 (m, 2H, C$_5$H$_3$); $^{13}$C-NMR (300 MHz, C$_6$D$_6$, 20° C., TMS): δ2.9 (SiMe$_2$), 3.0 (SiMe$_2$), 35.6 (N$^t$Bu), 45.1 (NMe$_2$), 55.8 (N$^t$Bu$_{ipso}$), 117.7 (C$_5$H$_{3ipso}$) 119.8 (C$_5$H$_3$), 133.2 (C$_5$H$_3$).

Preparation of [Zr{$\eta^5$-C$_5$H$_3$[SiMe$_2$(NHBu$^t$)][SiMe$_2$($\eta^t$-NBu$^t$)}(CH$_2$Ph)$_2$] (4)

A solution of Zr(CH$_2$Ph)$_4$ (2.93 g, 6.43 mmol) in toluene (70 ml) was cooled to 0° C. and 1 (2.09 g, 6.43 mmol) was added by syringe. The resulting yellow solution was warmed to 45° C. for 5 h. The solvent was removed under vacuum and the residue was extracted into pentane (70 ml). After filtration and removal of the solvent a mixture of complexes 4 and 5 was isolated. Formation of 4 was confirmed by IR and NMR spectroscopy although pure 4 free of 5 could not be isolated. IR (Nujol): ν=3353 cm$^{-1}$ (N—H). $^1$H-NMR (300 MHz, C$_6$D$_6$, 20° C., TMS) for 4: δ0.33 (s, 3H, SiMe$_2$), 0.34 (s, 3H, SiMe$_2$), 0.35 (s, 3H, SiMe$_2$), 0.40 (s, 3H, SiMe$_2$), 0.69 (s, 1H, NH$^t$Bu), 1.06 (s, 9H, NH$^t$Bu), 1.13 (s, 9H, N$^t$Bu), 1.66 (s, 1H, CH$_2$Ph), 1.72 (s, 1H, CH$_2$Ph), 2.12 (s, 1H, CH$_2$Ph), 2.17 (s, 1H, CH$_2$Ph), 6.21 (m, 1H, C$_5$H$_3$), 6.35 (m, 1H, C$_5$H$_3$), 6.60 (m, 1H, C$_5$H$_3$), 6.90–7.30 (m, 10H, C$_6$H$_5$). $^{13}$C-NMR (300 MHz, C$_6$D$_6$, 20° C., TMS): δ1.3 (SiMe$_2$), 2.4 (SiMe$_2$), 2.5 (SiMe$_2$), 2.8 (SiMe$_2$), 33.7 (NH$^t$Bu), 33.8 (N$^t$Bu), 49.7 (NH$^t$Bu$_{ipso}$), 54.9 (CH$_2$Ph), 57.1 (N$^t$Bu$_{ipso}$), 57.9 (CH$_2$Ph), 109.6 (C$_5$H$_{3ipso}$), 122.2 (C$_5$H$_3$), 122.5 (C$_5$H$_3$), 124.2 (C$_5$H$_3$), 125.6 (C$_5$H$_3$), 125.9 (C$_6$H$_5$), 126.4 (C$_6$H$_5$), 126.6 (C$_6$H$_5$), 127.8 (C$_6$H$_5$), 129.3 (C$_6$H$_5$), 129.6 (C$_6$H$_5$), 129.6 (C$_6$H$_5$), 129.8 (C$_6$H$_5$), 131.9 (C$_6$H$_5$), 145.8 (C$_6$H$_{5ipso}$), 146.2 (C$_6$H$_{5ipso}$).

Preparation of [Zr{$\eta^5$-C$_5$H$_3$-1,3-[SiMe$_2$($\eta^1$-NBu$^t$)]$_2$}(CH$_2$Ph)] (5)

A solution of Zr(CH$_2$Ph)$_4$ (2.93 gr, 6.43 mmol) in toluene (70 ml) was cooled to 0° C. and 1 (2.09 g, 6.43 mmol) was added by syringe. The resulting yellow solution was refluxed for 5 h. The solvent was removed under vacuum and the residue was extracted into pentane (70 ml). After filtration and removal of the solvent complex 5 was isolated as a brown oil. (3.20 g, 6.34 mmol, 99%). $^1$H-NMR (300 MHz, C$_6$D$_6$, 20° C., TMS): δ0.40 (s, 6H, SiMe$_2$), 0.42 (s, 6H, SiMe$_2$), 1.27 (s, 18H, N$^t$Bu), 2.12 (s, 2H, CH$_2$Ph), 6.14 (m, 1H, C$_5$H$_3$), 6.53 (m, 2H, C$_5$H$_3$) 6.9–7.23 (m, 5H, C$_6$H$_5$). $^{13}$C-NMR (300 MHz, C$_6$D$_6$, 20° C., TMS): δ2.4 (SiMe$_2$), δ2.4 (SiMe$_2$), 35.8 (N$^t$Bu), 55.7 (CH$_2$Ph), 57.1 (N$^t$Bu$_{ipso}$), 116.5 (C$_5$H$_{3ipso}$), 120.7 (C$_5$H$_3$), 126.4 (C$_5$H$_3$), 128.5 (C$_6$H$_5$), 129.8 (C$_6$H$_5$), 132.7 (C$_6$H$_5$), 150.6 (C$_6$H$_{5ipso}$). Anal. Found: C 57.01; H, 7.65; N, 5.48. Calc.:C, 57.20; H, 8.00; N, 5.56.

Preparation of [Ti{$\eta^5$-C$_5$H$_3$[SiMe$_2$(NHBu$^t$)][SiMe$_2$($\eta^1$-NBu$^t$)}(CH$_2$Ph)$_2$] (6)

A solution of Ti(CH$_2$Ph)$_4$ (2.14 g, 5.2 mmol) in toluene (70 ml) was cooled to 0° C. and 1 (1.69 g, 5.2 mmol) was added by syringe. The resulting yellow solution was warmed to 65° C. for 5 h. When evolution of gas stopped the solvent was removed under vacuum and the residue was extracted into pentane (70 ml). After filtration and removal of the solvent complex 6 was isolated as a red solid. (2.87 g, 5.2 mmol, 100%). $^1$H-NMR (300 MHz, C$_6$D$_6$, 20° C., TMS): δ0.21 (s, 3H, SiMe$_2$), 0.27 (s, 3H, SiMe$_2$), 0.37 (s, 3H, SiMe$_2$), 0.38 (s, 3H, SiMe$_2$), 0.72 (s, 1H, NH$^t$Bu), 1.07 (s, 9H, NH$^t$Bu), 1.44 (s, 9H, N$^t$Bu), 2.47 (d, 2H, J=10.5 Hz, CH$_2$Ph), 2.55 (d, 2H, J=10.5 Hz, CH$_2$Ph), 2.81 (d, 2H, J=10.5 Hz, CH$_2$Ph), 2.97 (d, 2H, J=10.5 Hz, CH$_2$Ph), 5.83 (m, 1H, C$_5$H$_3$), 6.14 (m, 1H, C$_5$H$_3$), 6.83 (m, 1H, C$_5$H$_3$), 6.87–7.20 (m, 10H, CH$_2$Ph); $^{13}$C-NMR (300 MHz, C$_6$D$_6$, 20° C., TMS): δ0.6 (SiMe$_2$), 1.5 (SiMe$_2$), 2.4 (SiMe$_2$), 2.9 (SiMe$_2$), 33.8 (NH$^t$Bu), 34.3 (N$^t$Bu), 49.8 (NH$^t$Bu$_{ipso}$), 61.5 (N$^t$Bu$_{ipso}$), 79.6 (CH$_2$Ph), 83.7 (CH$_2$Ph), 110.2 (C$_5$H$_{3ipso}$), 122.1 (C$_5$H$_3$), 122.5 (C$_5$H$_3$), 123.0 (C$_5$H$_3$), 125.9 (C$_5$H$_3$), 126.8 (C$_6$H$_5$), 126.8 (C$_6$H$_5$), 127.4 (C$_6$H$_5$), 128.5 (C$_6$H$_5$), 128.6 (C$_6$H$_5$), 128.7 (C$_6$H$_5$), 128.9 (C$_6$H$_5$), 129.8 (C$_6$H$_5$), 132.6 (C$_6$H$_5$), 149.6 (C$_6$H$_{5ipso}$), 150.1 (C$_6$H$_{5ipso}$). IR(nujol); ν=3349 cm$^{-1}$(N—H). Anal. Found: C, 62.58; H, 8.75; N, 6.08; Calc.: C, 62.68; H, 8.68; N, 5.76.

Preparation of [Ti{$\eta^5$-C$_5$H$_3$-1,3-[SiMe$_2$($\eta^1$-NBu$^t$)]$_2$}(CH$_2$Ph)] (7)

A solution of Ti(CH$_2$Ph)$_4$ (5.34 g, 12.9 mmol) in toluene (70 ml) was cooled to 0° C. and 1 (4.21 g, 12.9 mmol) was added by syringe. The resulting deep red solution was refluxed for 5 h. The solvent was removed under vacuum and the residue was extracted into pentane (70 ml). After filtration and removal of the solvent complex 7 was isolated as a deep red solid. (5.93 g, 12.9 mmol, 100%). $^1$H-NMR (300 MHz, C$_6$D$_6$, 20° C., TMS): δ0.39 (s, 6H, SiMe$_2$), 0.40 (s, 6H, SiMe$_2$), 1.42 (s, 18H, N$^t$Bu), 2.61 (s, 2H, CH$_2$Ph), 6.14 (m, 2H, C$_5$H$_3$), 6.40 (m, 1H, C$_5$H$_3$), 6.89 (m, 1H, C$_6$H$_5$), 7.00 (m, 2H, C$_6$H$_5$), 7.22 (m, 2H, C$_6$H$_5$); $^{13}$C-NMR (300 MHz, C$_6$D$_6$, 20° C., TMS): δ2.1 (SiMe$_2$), 2.2 (SiMe$_2$), 35.6 (N$^t$Bu), 59.3 (N$^t$Bu$_{ipso}$), 69.6 (CH$_2$Ph), 117.7 (C$_5$H$_{3ipso}$), 121.5 (C$_5$H$_3$), 126.3 (C$_5$H$_3$), 128.5 (C$_6$H$_5$), 130.3 (C$_6$H$_5$), 132.6 (C$_6$H$_5$), 152.4 (C$_6$H$_{5ipso}$). Anal. Found: C, 67.36; H, 8.75; N, 5.07. Calc.: C, 67.82; H, 8.71; N, 4.81.

Preparation of [Zr{$\eta^5$-C$_5$H$_3$-1,3-[SiMe$_2$($\eta^1$-NBu$^t$)]$_2$}]$^+$[(CH$_2$Ph)B(C$_6$F$_5$)$_3$]$^-$ (8)

A toluene (20 m) solution of the monobenzyl complex 5 (0.116 g, 0.25 mmol) was treated with B(C$_6$F$_5$)$_3$ (0.126 g, 0.25 mmol) at room temperature and the mixture was stirred for 30 m and cooled to −35° C. The solvent was filtered off from the resulting insoluble residue which was then dried under vacuum to give 8 (0.21 g, 83% yield) as a dark brown oil. $^1$H-NMR (300 MHz, C$_6$D$_6$, 20° C., TMS): δ0.17 (s, 6H, SiMe$_2$), 0.36 (s, 6H, SiMe$_2$), 0.99 (s, 18H, N$^t$Bu), 3.42 (s, 2H, BCH$_2$), 5.20 (m, 1H, C$_5$H$_3$), 6.01 (m, 2H, C$_5$H$_3$), 6.10 (m, 1H, p-C$_6$H$_5$), 6.34 (m, 2H, m-C$_6$H$_5$), 6.87 (m, 2H, o-C$_6$H$_5$). $^{13}$C-NMR (300 MHz, C$_6$D$_6$, 20° C. TMS): δ1.5 (SiMe$_2$), 1.6 (SiMe$_2$), 34.8(N$^t$Bu), 58.6 (N$^t$Bu$_{ipso}$), 121.4 (C$_5$H$_{3ipso}$) 127.4 (C$_5$H$_3$), 127.5 (C$_5$H$_3$), 127.9 (C$_6$H$_5$), 128.1 (C$_6$H$_5$), 128.3 (C$_6$H$_5$), 136.5 (C$_6$F$_5$), 138.3 (C$_6$F$_5$), 147.8 (C$_6$F$_5$), 149.8 (C$_6$F$_5$), 162.0 (C$_6$H$_{5ipso}$) $^{19}$F-NMR (300 MHz, C$_6$D$_6$, 20° C., CCl$_3$F); 132.1 (m, 2F, o-C$_6$F$_5$), 163.6 (m, 1F, p-C$_6$F$_5$), 167.2 (m, 2F, m-C$_6$F$_5$).

Preparation of [Ti{$\eta^5$-C$_5$H$_3$-1,3-[SiMe$_2$($\eta^1$-NBu$^t$)]$_2$}]$^+$[(CH$_2$Ph)B(C$_6$F$_5$)$_3$]$^-$ (9)

A toluene (20 ml) solution of the monobenzyl complex 7 (0.125 g, 0.25 mmol) was treated with B(C$_6$F$_5$)$_3$ (0.126 g, 0.25 mmol) at room temperature and the mixture was stirred for 30 m and cooled to −35° C. The solvent was filtered off from the resulting insoluble residue which was then dried under vacuum to give 9 (0.13 g, 60% yield) as an orange crystalline solid. $^1$H-NMR (300 MHz, C$_6$D$_6$, 20° C., TMS): δ0.19 (s, 6H, SiMe$_2$), 0.38 (s, 6H, SiMe$_2$), 1.12 (s, 18H, N$^t$Bu), 3.49 (s, 2H, BCH$_2$), 5.03 (m, 1H, C$_5$H$_3$), 5.86 (m, 2H, C$_5$H$_3$), 6.21–7.10 (m, 5H, C$_6$H$_5$). Compound 9 was only slightly soluble in C$_6$D$_6$, and its $^{13}$C NMR spectrum could not be recorded. $^{19}$F-NMR (300 MHz, C$_6$D$_6$, 20° C., CCl$_3$F): 132.1 (m, 2F, o-C$_6$F$_5$), 163.6 (m, 1F, p-C$_6$F$_5$), 167.2 (m, 2F, m-C$_6$F$_5$).

Polymerization of Ethylene

EXAMPLE 1
Ethylene Homopolymer by the use of the Compound 5

In a 1.3 l glass reactor were added 600 ml of dry heptane. The reactor was pressurized with 4 atm ethylene and then 12.9 ml methylaluminoxane (MAO, 1.5 M in toluene) and 4.2 micromoles of compound 5 dissolved in 5 ml toluene were added. The reactor is kept under stirring and therrnostated at 70° C. After 15', the polymerization was stopped by addition of acidified methanol. 2.96 g of polyethylene were obtained. The activity of the catalyst system was 740 kg PE/mol Zr·h·atm; Mw=541.000, Mw/Mn=1.9.

EXAMPLE 2
Ethylene-hexene Copolymers by the use of Compound 5

In a 1.3 l glass reactor were added 600 ml of dry heptane. The reactor was pressurized with 4 atm ethylene. 10 ml of previously distilled hexene were added, followed by 6.4 ml MAO (1.5 M in toluene) and 2.1 micromoles of compound 5 dissolved in 5 ml toluene.

The reactor is kept under stirring and therrnostated at 70° C. After 1 h, the polymerization was stopped by addition of acidified methanol. 1.81 g of polyethylene were obtained. The activity of the catalyst system was 226 kg PE/mol Zr·h·atm; Mw=440.000; Mw/Mn=2.6 and 0.7 mol % of hexene in the polymer.

EXAMPLE 3
Ethylene-hexene Copolymers by the use of Compound 5

Example 2 was repeated but using 12.9 ml of MAO and 4.2 micromoles of compound 5. After 30' of polymerization 2.78 g of polyemer were obtained. The activity of the catalyst system was 348 kg PE/mol Zr·h·atm; Mw=408.000; Mw/Mn=2.2 and 0.7 mol % of hexene in the polymer.

Polymerization of Propylene

EXAMPLE 4
Propylene Homopolymer by the use of the Compound 5

In a 1.3 l glass reactor were added 600 ml of dry heptane. The reactor was pressurized with 5 atm propylene and then 0.01 mmol of compound 5 in 15 ml MAO (1.5 M in toluene) were added. The reactor was kept under stirring and thermostated at 40° C. After 1 h, the polymerization was stopped by addition of acidified methanol. The solvent was removed by using a rotavapor. The residue was washed with methanol and the polymer is then dried. 2.4 g of atactic polypropylene (according to $^{13}$C NMR) were obtained.

EXAMPLE 5
Propylene Homopolymer by the use of the Compound 5

In a 1.3 l glass reactor were added 600 ml of dry heptane. The reactor was pressurized with 5 atm propylene. 4.65 ml MAO (1.5 Min toluene) were added and then 0.01 mmol of compound 5 in 5 ml MAO (1.5 M in toluene) were added. The reactor was kept under stirring and thermostated at 70° C. After 1 h, the polymerization was stopped by addition of acidified methanol. The solvent was removed by using a rotavapor. The residue was washed with methanol and the polymer is then dried. 3.0 g of atactic polypropylene (according to $^{13}$C NMR) were obtained.

Polymerization of Styrene

EXAMPLE 6
Polystyrene Homopolymer by the use of the Compound 5

A 500 mL bottle containing a stirring bar, closed with a crown cap and equipped with a septum was purged with $N_2$. Cyclohexane (100 mL) and styrene (0,4 mol) was added, followed by MAO (11 mL) and compound 5 (0,017 mmol) dissolved in toluene (3 mL). The system was immersed in a thermostatic bath at 60° C. and the mixture was stirred during 180 min. After this time the polymerization was stopped by addition of acidified methanol. The solvent was removed by using a rotavapor. The residue was washed with methanol and the polymer was then dried. 1,56 g of atactic polystyrene (according to $^1$H NMR) were obtained.

EXAMPLE 7
Polystyrene Homopolymer by the use of the Compound 5

A 500 mL bottle containing a stirring bar, closed with a crown cap and equipped with a septum was purged with $N_2$. Cyclohexane (100 mL) and styrene (0.4 mol) was added, followed by MAO (11 mL) and compound 5 (0,034 mmol) dissolved in toluene (6 mL). The system was immersed in a thermostatic bath at 60° C. and the mixture was stirred during 180 min. After this time the polymerization was stopped by addition of acidified methanol. The solvent was removed by using a rotavapor. The residue was washed with methanol and the polymer was then dried. 1,63 g of atactic polystyrene (according to $^1$H NMR) were obtained.

What is claimed is:

1. Olefin polymerization catalyst component comprising an organometallic compound of general formula (I)

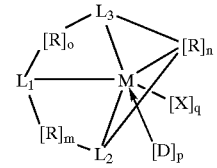

(I)

wherein

M is a transition metal selected from the group consisting of groups 3, 4–10, lanthanide, and actinide of the periodic table of the elements;

each R is independently a structural bridge rigidly connecting two ligands $L_1$, $L_2$ and $L_3$ and is constituted by 1 to 4 chain atoms selected from the group consisting of carbon, silicon, germanium, oxygen, and boron;

m, n and o are 0 or 1, with the proviso that m+n+o is 2 or 3;

$L_1$ is a ligand of the cyclopentadienyl-type ligand or is isolobal to cyclopentadienyl;

$L_2$ is a ligand of the cyclopentadienyl-type ligand, is isolobal to cyclopentadienyl, or is a monovalent anionic ligand selected from the group consisting of N, P, and B when m+n=2, or $L_2$ is selected from the group consisting of $NR^1$, $PR^1$, $BR^1$, O and S when m+n=1;

$L_3$ is a monovalent anionic ligand selected from the group consisting of N, P, and B when n+o=2, $L_3$ is selected from the group consisting of $NR^1$, $PR^1$, $BR^1$, O and S when n+o=1;

$R^1$ is hydrogen, $C_1$–$C_{20}$ alkyl, $C_3$–$C_{20}$ cycloalkyl, $C_6$–$C_{20}$ aryl, or $C_3$–$C_{20}$ alkenyl, optionally comprising 1 to 5 heteroatoms selected from the group consisting of Si, N, P, O, F, Cl, and Br;

each X is independently selected from the group consisting of hydrogen, halogen, $NR^2_2$, and $R^2$, wherein $R^2$ is equal to $C_1$–$C_{20}$ alkyl, $C_3$–$C_{20}$ cycloalkyl, $C_6$–$C_{20}$ aryl, or $C_3$–$C_{20}$ alkenyl optionally comprising 1 to 5 heteroatoms selected from the group consisting of Si, N, P, O, F, Cl, and Br;

q is a number whose value is: 0, 1, 2 or 3, depending on a valency of the metal M;

D is a neutral Lewis base; and p is a number whose value is 0, 1, 2 or 3.

2. Catalyst component according to claim 1 wherein n is 0 and each R is independently selected from the group consisting of $CR^1_2$, $SiR^1_2$, $CR^1_2$—$CR^1_2$, $CR^1_2$—$SiR^1_2$, $SiR^1_2$—$SiR^1_2$; wherein each $R^1$ is independently selected from the group consisting of hydrogen, $C_1$–$C_{20}$ alkyl, $C_3$–$C_{20}$ cycloalkyl, $C_6$–$C_{20}$ aryl, and $C_3$–$C_{20}$ alkenyl, optionally comprising 1 to 5 heteroatoms selected from the group consisting of Si, N, P, O, F, Cl, and Br.

3. Catalyst component according to claim 1 wherein D is selected from the group consisting of linear ethers, cyclic ethers, amines, and phosphines.

4. Catalyst component according to claim 1 wherein the organometallic compound has formula (II)

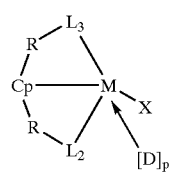

(II)

wherein Cp is a cyclopentadienyl or indenyl ring, optionally substituted by one or more $R^1$ groups, and M is selected from the group consisting of Ti, Zr and Hf;

each R is independently selected from the group consisting of $CR^1_2$, $SiR^1_2$, $CR^1_2$—$CR^1_2$, $CR^1_2$—$SiR^1_2$, and $SiR^1_2$—$SiR^1_2$, wherein $R^1$ is hydrogen, $C_1$–$C_{20}$ alkyl, $C_3$–$C_{20}$ cycloalkyl, $C_6$–$C_{20}$ aryl, or $C_3$–$C_{20}$ alkenyl, optionally comprising 1 to 5 heteroatoms selected from the group consisting of Si, N, P, O, F, Cl, and Br;

$L_2$ and $L_3$ are independently selected from the group consisting of $NR^1$, $PR^1$, $BR^1$, O and S;

X is independently selected from the group consisting of hydrogen, halogen, $NR^2_2$, $R^2$ wherein $R^2$ is equal to $C_1$–$C_{20}$ alkyl, $C_3$–$C_{20}$ cycloalkyl, $C_6$–$C_{20}$ aryl, or $C_3$–$C_{20}$ alkenyl, optionally comprising 1 to 5 heteroatoms selected from the group consisting of Si, N, F, O, F, Cl, and Br;

D is a neutral Lewis base; and p is a number whose value is: 0, 1, 2 or 3.

5. Catalyst component according to claim 1 wherein o is equal to 0.

6. Catalyst component according to claim 1 wherein at least one group selected from $L_1$, $L_2$ and $L_3$ and/or one R group contains an —O—$SiR^2_3$ group.

7. Catalyst component comprising a compound according to claim 1 and a porous support.

8. Olefin polymerization catalyst comprising a catalyst compound according to claim 1 and a cocatalyst selected from the group consisting of aluminoxanes and boron Lewis acids.

9. Process for preparation of the catalyst component according to claim 1 comprising reacting a compound of formula $MX_{q+3}$ wherein M is a transition metal selected from the group consisting of groups 3, 4–10, lanthanide, and actinide of the periodic table of the elements, X is a monovalent anionic ligand, and q is 0, 1, 2, or 3 depending on a valence of the metal M, with a compound of formula (III)

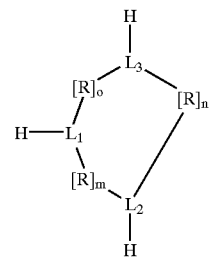

(III)

wherein each R is independently a structural bridge rigidly connecting two ligands $L_1$, $L_2$ and $L_3$ and is constituted by 1 to 4 chain atoms selected from the group consisting of carbon, silicon, germanium, oxygen, and boron; wherein these chain atoms optionally are part of fused rings, aromatic rings, or spiro rings;

m, n and o are 0 or 1, with the proviso that m+n+o is 2 or 3;

$L_1$ is a cyclopentadienyl-type group or is isolobal to cyclopentadienyl, optionally substituted by one or more $R^1$ groups;

$L_2$ is a cyclopentadienyl-type group, is isolobal to cyclopentadienyl, or is selected from the group consisting of N, P, and B when m+n=2, or $L_2$ is selected from the group consisting of $NR^1$, $PR^1$, $BR^1$, O and S when m+n=1;

$L_3$ is selected from the group consisting of N, P, and B when n+o=2, or $L_3$ is selected from the group consisting of $NR^1$, $PR^1$, $BR^1$, O and S when n+o=1; and $R^1$ is hydrogen, $C_1$–$C_{20}$ alkyl, $C_3$–$C_{20}$ cycloalkyl, $C_6$–$C_{20}$ aryl, or $C_3$–$C_{20}$ alkenyl, optionally comprising 1 to 5 heteroatoms selected from the group consisting of Si, N, P, O, F, Cl, and Br.

10. A compound of formula (III)

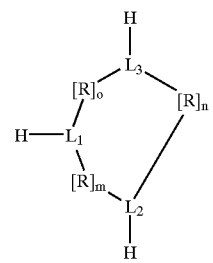

(III)

wherein each R is independently a structural bridge rigidly connecting two ligands $L_1$, $L_2$ and $L_3$ and is constituted by 1 to 4 chain atoms selected from the group consisting of carbon, silicon, germanium, oxygen, and boron; wherein these atoms optionally are part of fused rings, aromatic rings, or spiro rings;

m, n and o are 0 or 1, with the proviso that m+n+o is 2 or 3;

$L_1$ is a cyclopentadienyl-type group or is isolobal to cyclopentadienyl, optionally substituted by one or more groups;

$L_2$ is a cyclopentadienyl-type group or is isolobal to cyclopentadienyl, or is selected from the group consisting of N, P, and B when m+n=2, or $L_2$ is selected from the group consisting of NR$^1$, PR$^1$, BR$^1$, O and S when m+n=1;

L$_3$ is selected from the group consisting of N, P, and B when n+o=2 or L$_3$ is selected from the group consisting of NR$^1$, PR$^1$, BR$^1$, O and S when n+o=1; and R$^1$ is hydrogen, C$_1$–C$_{20}$ alkyl, C$_3$–C$_{20}$ cycloalkyl, C$_6$–C$_{20}$ aryl, or C$_3$–C$_{20}$ alkenyl, optionally comprising 1 to 5 heteroatoms selected from the group consisting of Si, N, P, O, F, Cl, and Br.

11. A process for preparing a polyolefin by comprising polymerizing olefins with the catalyst as claimed in claim 8 to yield the polyolefin.

12. A polyolefin obtained by the process of claim 11.

13. Catalyst component according to claim 1 wherein M is selected from the group consisting of titanium, zirconium, and hafnium.

14. Catalyst component according to claim 1 wherein L is a cyclopentadienyl, indenyl or fluorenyl ring, cyclopenteno[b]tiophenyl, cyclopenteno[b:b']-dithiophenyl, cyclopenteno[b]pyrrolyl, boratabenzene, phospholyl, dihydroindeno[b]indolyl, optionally substituted by one or more R$^1$ groups.

15. Catalyst component according to claim 1 wherein L is a cyclopentadienyl, indenyl or fluorenyl ring, optionally substituted by one or more R$^1$ groups.

16. Catalyst component according to claim 13 wherein L is a cyclopentadienyl, indenyl or fluorenyl ring, optionally substituted by one or more R$^1$ groups.

17. Catalyst component according to claim 13 wherein L is a cyclopentadienyl, indenyl or fluorenyl ring, cyclopenteno [b]tiophenyl, cyclopenteno[b:b']-dithiophenyl, cyclopenteno[b]pyrrolyl, boratabenzene, phospholyl, dihydroindeno[b]indolyl, optionally substituted by one or more R$^1$ groups.

18. Olefin polymerization catalyst component comprising an organometallic compound of general formula (I)

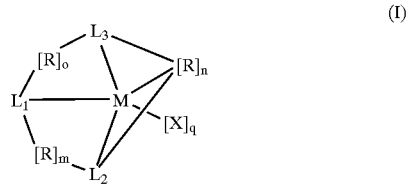

(I)

wherein

M is a transition metal selected from the group consisting of groups 3, 4–10, lanthanide, and actinide of the periodic table of the elements;

each R is independently a structural bridge rigidly connecting two ligands L$_1$, L$_2$ and L$_3$ and is constituted by 1 to 4 chain atoms selected from the group consisting of carbon, silicon, germanium, oxygen, and boron;

m, n and o are 0 or 1, with the proviso that m+n+o is 2 or 3;

L$_1$ is a cyclopentadienyl-type ligand or is isolobal to cyclopentadienyl;

L$_2$ is a cyclopentadienyl-type ligand, is isolobal to cyclopentadienyl, or is a monovalent anionic ligand selected from the group consisting of N, P, and B when m+n=2, or L$_2$ is selected from the group consisting of NR$^1$, PR$^1$, BR$^1$, O and S when m+n=1;

L$_3$ is a monovalent anionic ligand selected from the group consisting of N, P, and B when n+o=2, or L$_3$ is selected from the group consisting of NR$^1$, PR$^1$, BR$^1$, O and S when n+o=1;

R$^1$ is hydrogen, C$_1$–C$_{20}$ alkyl, C$_3$–C$_{20}$ cycloalkyl, C$_6$–C$_{20}$ aryl, or C$_3$–C$_{20}$ alkenyl, optionally comprising 1 to 5 heteroatoms selected from the group consisting of Si, N, P, O, F, Cl and Br;

each X is independently selected from the group consisting of hydrogen, halogen, NR$^2{}_2$, and R$^2$, wherein R$^2$ is equal to C$_1$–C$_{20}$ alkyl, C$_3$–C$_{20}$ cycloalkyl, C$_6$–C$_{20}$ aryl, or C$_3$–C$_{20}$ alkenyl, optionally comprising 1 to 5 heteroatoms selected from the group consisting of Si, N, P, O, F, Cl and Br; and q is a number whose value is: 0, 1, 2 or 3, depending on a valency of the metal M.

19. Catalyst component according to claim 18 containing [D]$_p$ wherein D is a neutral Lewis base and p is a number whose value is 0, 1, 2 or 3.

20. Catalyst component according to claim 18 wherein D is selected from the group consisting of linear ethers, cyclic ethers, amines, and phosphines.

21. Catalyst component according to claim 18 wherein the organometallic compound has formula (II)

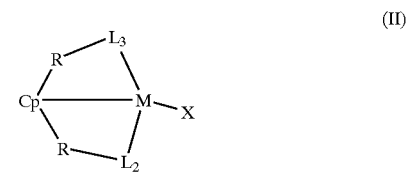

(II)

wherein Cp is a cyclopentadienyl or indenyl ring optionally substituted by one or more R$^1$ groups;

M is selected from the group consisting of Ti, Zr and Hf;

each R is independently selected from the group consisting of CR$^1{}_2$, SiR$^1{}_2$, CR$^1{}_2$—CR$^1{}_2$, CR$^1{}_2$—SiR$^1{}_2$, and SiR$^1{}_2$—SiR$^1{}_2$, wherein R$^1$ is hydrogen, C$_1$–C$_{20}$ alkyl, C$_3$–C$_{20}$ cycloalkyl, C$_6$–C$_{20}$ aryl, or C$_3$–C$_{20}$ alkenyl, optionally comprising 1 to 5 heteroatoms selected from the group consisting of Si, N, P, O, F, Cl, and Br;

L$_2$ and L$_3$ are independently selected from the group consisting of NR$^1$, PR$^1$, BR$^1$, O and S;

X is independently selected from the group consisting of hydrogen, halogen, NR$^2$, and R$^2$, wherein R$^2$ is equal to C$_1$–C$_{20}$ alkyl, C$_3$–C$_{20}$ cycloalkyl, C$_6$–C$_{20}$ aryl, or C$_3$–C$_{20}$ alkenyl, optionally comprising 1 to 5 heteroatoms selected from the group consisting of Si, N, P, O, F, Cl, and Br.

22. Catalyst component according to claim 21 containing [D]$_p$ wherein D is a neutral Lewis base and p is a number whose value is 0, 1, 2 or 3.

23. Catalyst component according to claim 21 wherein D is selected from the group consisting of linear ethers, cyclic ethers, amines, and phosphines.

24. Process for preparation of the catalyst component as claimed in claim 18 comprising reacting a compound of formula MX$_{q+3}$ wherein M is a transition metal selected from the group consisting of groups 3, 4–10, lanthanide, and actinide of the periodic table of the elements, X is a monovalent anionic ligand, and q is 0, 1, 2, or 3 depending on a valence of the metal M, with a compound of formula (III)

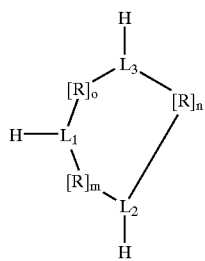

(III)

wherein
- each R is independently a structural bridge rigidly connecting two ligands $L_1$, $L_2$ and $L_3$ and is constituted by 1 to 4 chain atoms selected from the group consisting of carbon, silicon, germanium, oxygen, and boron; wherein these chain atoms optionally are part of fused rings, aromatic rings, or spiro rings;
- m, n and o are 0 or 1, with the proviso that m+n+o is 2 or 3;
- $L_1$ is a cyclopentadienyl-type group or is isolobal to cyclopentadienyl, optionally substituted by one or more $R^1$ groups;
- $L_2$ is a cyclopentadienyl-type group, is isolobal to cyclopentadienyl, or is selected from the group consisting of N, P, and B when m+n=2, or $L_2$ is selected from the group consisting of $NR^1$, $PR^1$, $BR^1$, O and S when m+n=1;
- $L_3$ is selected from the group consisting of N, P, and B when n+o=2, or $L_3$ is selected from the group consisting of $NR^1$, $PR^1$, $BR^1$, O and S when n+o=1; and
- $R^1$ is hydrogen, $C_1$–$C_{20}$ alkyl, $C_3$–$C_{20}$ cycloalkyl, $C_6$–$C_{20}$ aryl, or $C_3$–$C_{20}$ alkenyl, optionally comprising 1 to 5 heteroatoms selected from the group consisting of Si, N, F, O, F, Cl, and Br.

25. Catalyst component according to claim 1 wherein the organometallic compound of the formula (I) is selected from the group consisting of:

$[Zr\{\eta^5\text{-}C_5H_3[SiMe_2(NHBu')][SiMe_2(\eta^1\text{-}NBu')\}(NMe_2)_2]$, $[Zr\{\eta^5\text{-}C_5H_3\text{-}1,3\text{-}[SiMe_2(\eta^1\text{-}NBu')]_2)\}(NMe_2)]$, $[Zr\{\eta^5\text{-}C_5H_3[SiMe_2(NHBu')][SiMe_2(\eta^1\text{-}NBu')\}(CH_2Ph)_2]$, $[Zr\{\eta^5\text{-}C_5H_3\text{-}1,3\text{-}[SiMe_2(\eta^1\text{-}NBu')]_2\}(CH_2Ph)_2]$, $[Ti\{\eta^5\text{-}C_5H_3[SiMe_2(NHBU')][SiMe_2(\eta^1\text{-}NBu')\}(CH_2Ph)_2]$, and $[Ti\{\eta^5C_5H_3\text{-}1,3\text{-}[SiMe_2(\eta^1\text{-}NBu')]_2\}(CH_2Ph)]$.

26. Catalyst component according to claim 1 wherein the organometallic compound of the formula (I) is selected from the group consisting of:

$[Zr\{\eta^5\text{-}C_5H_3\text{-}1,3\text{-}[SiMe_2(\eta^1\text{-}NBu')]_2\}]^+[(CH_2Ph)B(C_6F_5)_3]^-$ and $[Ti\{\eta_5\text{-}C_5H_3\text{-}1,3\text{-}[SiMe_2(\eta^1\text{-}NBu')]_2\}]^+[(CH_2Ph)B(C_6F_5)_3]^-$.

* * * * *